US008241883B2

(12) United States Patent
Chow et al.

(10) Patent No.: US 8,241,883 B2
(45) Date of Patent: Aug. 14, 2012

(54) HIGH THROUGHPUT MOBILITY SHIFT

(75) Inventors: Andrea W. Chow, Los Altos, CA (US); John C. Owicki, Palo Alto, CA (US); J. Wallace Parce, Palo Alto, CA (US)

(73) Assignee: Caliper Life Sciences, Inc., Alameda, CA (US)

( * ) Notice: Subject to any disclaimer, the term of this patent is extended or adjusted under 35 U.S.C. 154(b) by 1366 days.

(21) Appl. No.: 11/412,055

(22) Filed: Apr. 25, 2006

(65) Prior Publication Data
US 2007/0099200 A1    May 3, 2007

Related U.S. Application Data

(62) Division of application No. 10/421,642, filed on Apr. 23, 2003, now abandoned.

(60) Provisional application No. 60/375,538, filed on Apr. 24, 2002.

(51) Int. Cl.
*C12N 13/00* (2006.01)

(52) U.S. Cl. ........ 435/173.1; 435/4; 435/6.19; 436/512; 436/517

(58) Field of Classification Search .......................... None
See application file for complete search history.

(56) References Cited

U.S. PATENT DOCUMENTS

| 5,122,248 | A | * | 6/1992 | Karger et al. ................. 204/453 |
| 5,271,724 | A | | 12/1993 | van Lintel |
| 5,277,556 | A | | 1/1994 | van Lintel |
| 5,375,979 | A | | 12/1994 | Trah |
| 5,800,690 | A | * | 9/1998 | Chow et al. ................... 204/451 |
| 5,880,071 | A | | 3/1999 | Parce et al. |
| 5,942,443 | A | | 8/1999 | Parce et al. |
| 5,965,410 | A | | 10/1999 | Chow et al. |
| 6,416,642 | B1 | | 7/2002 | Alajoki et al. |
| 6,458,259 | B1 | | 10/2002 | Parce et al. |
| 6,506,609 | B1 | | 1/2003 | Wada et al. |
| 6,524,790 | B1 | | 2/2003 | Kopf-Sill et al. |
| 6,551,836 | B1 | | 4/2003 | Chow et al. |
| 2001/0023825 | A1 | * | 9/2001 | Frumin et al. ................. 204/458 |
| 2001/0041357 | A1 | * | 11/2001 | Fouillet et al. ............... 435/91.1 |
| 2001/0052460 | A1 | | 12/2001 | Chien et al. |
| 2004/0219545 | A1 | * | 11/2004 | Rando et al. ....................... 435/6 |

FOREIGN PATENT DOCUMENTS

| WO | WO 94/05414 | 3/1994 |
| WO | WO 96/04547 | 2/1996 |
| WO | WO 97/02357 | 1/1997 |
| WO | WO 98/45481 | 10/1998 |
| WO | WO 98/46438 | 10/1998 |
| WO | WO 98/49548 | 11/1998 |

(Continued)

OTHER PUBLICATIONS

U.S. Appl. No. 09/993,314.

(Continued)

*Primary Examiner* — N. C. Yang
(74) *Attorney, Agent, or Firm* — Cardinal Law Group

(57) ABSTRACT

The present invention provides novel microfluidic devices and methods for performing pulsed field mobility shift assays in microfluidic devices. In particular the devices and methods of the invention utilize differences between electrophoretic mobilities (e.g., as between reactants and products, especially in non-fluorogenic reactions) in order to separate the species and thus analyze the reaction.

32 Claims, 7 Drawing Sheets

FOREIGN PATENT DOCUMENTS

WO      WO 99/64836      12/1999

OTHER PUBLICATIONS

U.S. Appl. No. 10/202,487.

A. R. Kopf-Sill, T. Nikiforov, L. Bousse, R. Nagel, & J. W. Parce in Proceedings of Micro- and Nanofabricated Electro-Optical Mechanical Systems for Biomedical and Environmental Applications, SPIE, vol. 2978, San Jose, California, Feb. 1997, p. 172-179.

Kopp, M. et al. (1998) "Chemical amplification: continuous-flow PCR on a chip" Science 280(5366):1046-1048.

Song et al., "Multisample Analysis Using an Array of Microreactors for an Alternating-Current Field-Enhanced Latex Immunoassay", Anal. Chem. 1994, 66, 778-781 (1994).

* cited by examiner

HIGH THROUGHPUT MOBILITY SHIFT

CROSS-REFERENCE TO RELATED APPLICATION

This application is a divisional of U.S. Utility patent application Ser. No. 10/421,642 filed Apr. 23, 2003, which claims the benefit of U.S. Provisional Patent Application No. 60/375,538, filed Apr. 24, 2002, which is incorporated herein by reference in its entirety for all purposes.

FIELD OF THE INVENTION

The present invention provides microfluidic devices and methods for the high throughput detection and characterization of interaction of at least two molecules in a microfluidic device based upon the molecules' differing electrophoretic mobility.

BACKGROUND OF THE INVENTION

When carrying out processes such as chemical or biochemical analyses, assays, syntheses, or preparations, a large number of separate manipulations are performed on the materials being processed. These manipulations include the measuring, aliquotting, transferring, diluting, mixing, separating, detecting, and incubating of the materials. Microfluidic technology miniaturizes these manipulations and integrates them so that they can be executed within a single microfluidic device. For example, pioneering microfluidic methods of performing biological assays in microfluidic systems have been developed, such as those described in U.S. Pat. No. 5,942,443 entitled "High Throughput Screening Assay Systems in Microscale Fluidic Devices" by Parce et al. and in PCT Published Application Number WO 98/45481 entitled "Closed Loop Biochemical Analyzers" by Knapp et al.

A problem of particular interest in numerous applications of microfluidic devices is the detection, characterization, and quantification of reactions that cannot be conveniently monitored by taking fluorogenic measurements. Such reactions include reactions in which there is no measurable change in fluorescence when a reaction product is formed. For example, kinase reactions have no easy fluorogenic means of quantification. Mobility shift assays in microfluidic devices were devised to help overcome this problem. Mobility shift assays are described in U.S. Pat. No. 6,524,790 entitled "Apparatus and Methods for Correcting for Variable Velocity in Microfluidic Systems," by Kopf-Sill et al.

The mobility shift assays currently carried out in microfluidic devices could be improved by increasing the throughput of those assays, and by expanding the applicability of those assays to reactions not compatible with existing mobility shift assays. The throughputs of some existing mobility shift assays are adversely affected by the long transit times required to separate some molecules based upon their electrophoretic mobility. These long transit times can lead to increased thermal dispersion of the separated groups of molecules, as well as hydrodynamically induced dispersion when pressure driven flow is used. Dispersion can adversely affect the throughput rate of an assay and decrease separation resolution. Accordingly, minimizing the transit times in a mobility shift assay can increase the throughput and improve the resolution of an assay.

A welcome addition to the art would be the enhanced ability to increase the throughput and resolution of mobility shift assays by decreasing the transit time. The present invention describes and provides these and other features by providing new methods and microfluidic devices that meet these and other goals.

SUMMARY OF THE INVENTION

The present invention provides methods, systems, kits, and devices for detection and characterization of interactions of molecules in a microfluidic device based upon the molecules' differing electrophoretic mobility in a pulsed electric field. Molecules to be assayed are flowed through one or more microchannels and subjected to a pulsed electric field. The molecules are then detected and their interactions are characterized.

In one aspect, the invention comprises a method of detecting an interaction between a first molecule and at least a second molecule in a microfluidic device involving flowing a first molecule that has a first electrophoretic mobility and is labeled with a first label together with at least a second molecule that has a second electrophoretic mobility and is optionally labeled with the same or a different label than the first molecule, applying a pulsed electric field through the microchannel to separate the first and at least second molecules based upon their electrophoretic mobilities, and detecting levels of label (or levels of signal from labels) in the microchannel over a select period of time to determine the interaction (if any) between the molecules. In some embodiments the at least second molecule comprises a second molecule and at least a third molecule. Embodiments of the invention may be employed to assay molecular interactions in which the first and second molecules interact to form the third molecule. These types of molecular interactions occur between receptors and ligands (where the third molecule comprises the receptor-ligand pair), antibodies and antigens (where the third molecule is an antibody-antigen complex), two at least partially complementary nucleic acid strands (where the third molecule comprises the resulting double-stranded nucleic acid), and enzymes and substrates (where the third molecule comprises the product). In the case of enzyme/substrate interactions, the product may comprises the label(s) from the first (or in some situations the second) molecule, and also may comprise the first molecule with a changed electrophoretic mobility. In some embodiments of methods in accordance with the invention, the at least second molecule may comprise a derivative form of the first molecule.

In some embodiments, the method of detecting an interaction between a first molecule and at least a second molecule further involves at least a fourth molecule that can be one or more of a reaction enhancer, a reaction inhibitor, or a reaction competitor. Additionally, in some embodiments one or more of the molecules being assayed optionally changes one or more of its size, charge, or electrophoretic mobility during or after the interaction of the molecules. The interaction of the molecules in the assays of embodiments of the invention optionally comprise an enzymatic reaction or a binding reaction.

In methods in accordance with the invention, the flow of molecules through one or more microchannels may be one or more of electrophoretic flow, electroosmotic flow, pressure based flow, wicking based flow, or hydrostatic pressure based flow. The flow of the molecules can also be optimized to increase assay sensitivity by, for example, increasing or maximizing the difference in a reaction parameter as compared between when the pulsed electric field is in a first state (e.g., on, or at a first value) and in a second state (e.g., off, or at a second value). Flowing can also comprise incubating the molecules being assayed, such as the first and second molecules, for a specific period of time. In other embodiments, flowing the molecules comprises continuously injecting a first molecule into the microchannel and intermittently injecting the at least second molecule into the same microchannel. The intermittent injection optionally comprises a length of time at least as long as the period of a pulse in the electric field. In various embodiments, the molecules to be interacted, typically the first and second molecules, are both continuously flowed into/through the microchannel either concurrently or non-concurrently, or are both intermittently flowed into/through the microchannel where the flows of the different molecules are completely or partially overlapping.

In various embodiments of the methods of the invention, the label of one or more of the molecules in the assay comprises a fluorescent label, a chemiluminescent label, or a radioactive label. Furthermore, detecting of the components of the pulsed field assay can optionally include determination of reaction kinetics between the first and at least second molecule.

In some embodiments of the methods of the invention, the electrophoretic mobility of the first molecule is greater than that of the second molecule, while in other embodiments, the electrophoretic mobility of the first molecule is less than that of the second molecule.

The application of a pulsed electric field in methods in accordance with the invention optionally comprises a first state comprising applying an electric field that produces a first specific voltage or electric current through the microchannel for a first specific period of time followed by a second state comprising applying an electric field that produces a second specific voltage or electric current for a second specific period of time. Such first and second periods of time are optionally equal and in some embodiments range from about 0.1, 0.2, 0.3, 0.4, 0.5, 1, 2, 3, 4, 5, 10, 15, or 20 seconds or more, or any length in between. Alternatively, in some embodiments such periods of time are not of equal length and can different by a factor of 1, 2, 3, 4, 5, 10, 20, 25, 30, 35, 40, 45, 50 or more, or any non-integral factor in between. In exemplary embodiments, the magnitude of the pulsed fields that produce the first and second specific voltages or electric currents can range from at least about 10 V/cm to about 3,000 V/cm or more, from at least about 50 V/cm to about 2,000 V/cm or more, from at least about 100 V/cm to at least about 1,000 V/cm or more, or from at least about 250 V/cm to at least about 750 V/cm or more.

In embodiments wherein a first molecule is continuously injected into the microchannel and a second or more molecule is intermittently injected into the microchannel, the periods of time when the pulsed field is at a first value and then at a second value are optionally selectively set in relation to the periods of time the second molecule is flowed into the microchannel, which comprises a third period of time. Such third period of time can optionally be from about 1 to about 100 or more times longer than the first and/or second periods of time. Alternatively, the third period of time can be at least about 5 to at least about 75, from at least about 10 to at least about 50, or from at least about 25 to at least about 45 times longer than the first and/or second periods of time.

In some embodiments, the microchannel in which the pulsed field assay is performed can optionally comprise a polymer gel, a microfabricated barrier, or a sieving matrix.

In some aspects, embodiments of the current invention comprise an integrated system or microfluidic device for detecting an interaction between a first molecule and at least a second molecule. Embodiments of such systems or devices include a body structure with at least a first microchannel disposed therein, a source of a first labeled molecule with a first electrophoretic mobility fluidly coupled to the microchannel, a source of at least a second molecule with a second electrophoretic mobility fluidly coupled to the microchannel, a fluid direction system that controllably moves the first and second molecules through the microchannel; a voltage regulator system that controllably applies a pulsed electric field through the microchannel wherein the pulsed field separates the molecules based upon their electrophoretic mobilities, a detector system to detect the level(s) of label(s) or the level of signal from label(s) in the microchannel over time, and system software comprising logical instructions to determine the interaction between the molecules based upon the electrophoretic mobility of the molecules in the pulsed electric field.

In various embodiments, the sources of the first and second molecules may comprise the same or different sources. Additionally, the flow effectuated by the fluid direction system optionally comprises one or more of electrokinetic flow, pressure driven flow, wicking driven flow, and hydrostatic pressure driven flow. Such flow optionally includes a continuous flow of the first molecule and an intermittent flow of the second molecule; a continuous flow of both molecules; an intermittent flow of both molecules; or an intermittent flow of the first molecule and a continuous flow of the second molecule. Additionally, the fluid direction system optionally optimizes assay sensitivity by maximizing or increasing the difference in one or more reaction parameters where such parameters are compared between when the pulsed field is in a first state and when the pulsed field is in a second state. The fluid direction system also optionally provides for incubating the first and the second molecules together for a specific period of time.

In some embodiments, the voltage regulator system of the a system or device in accordance with the invention applies a pulsed electric field comprising a first state in which an electric field produces a specific voltage or electric current in the microchannel for a first specific controllable period of time followed by a second state in which the electric field is not applied for a second specific controllable period of time. Alternatively, in the first state a first electric field is applied that produces a first voltage or first current at a first level in the microchannel for a first period of time, and in the second state a second electric field is applied that produces a second voltage or second current at a second level for a second period of time. Such periods of time are optionally determined based upon the rate of injection of the first or second molecule into the microchannel, or upon the intermittent flow of the second molecule. Integrated systems or devices in accordance with the invention optionally detect one or more of fluorescence, chemiluminescence, or radiation from the molecules in the microchannel.

Many additional aspects of the invention will be apparent upon complete review of this disclosure, including uses of devices and systems in accordance with the invention, methods of manufacture of devices and systems in accordance with the invention, and kits for practicing methods in accordance with the invention. For example, kits comprising embodiments of any devices or systems for performing one or more pulsed field mobility shift assay in accordance with the invention, or elements thereof, in conjunction with packaging materials (e.g., containers, or sealable plastic bags) and instructions for using the devices to practice the methods herein, are also contemplated.

DETAILED DISCUSSION OF THE INVENTION

Figure 1A:
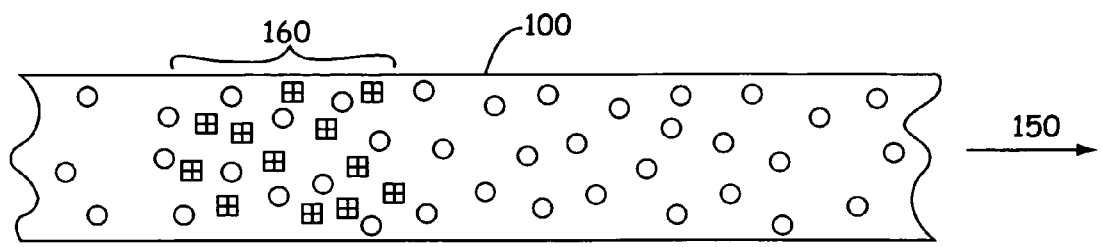
FIG. 1, panels A and B, schematically illustrate a microchannel containing areas of higher and lower fluorescence resulting from the increased mobility of a labeled product.

The methods and devices of the current invention increase the throughput of mobility shift assays carried out in microfluidic devices. Briefly, the invention provides devices and methods that can increase the throughput rate of assays comprising the electrophoretic separation of materials through the application of a pulsed electric field that provides specific pulses of voltage and/or electric current through a microchannel in the microfluidic device.

Methods and devices in accordance with the current invention can be used to perform pulsed field mobility shift assays for a variety of applications. For example, methods and devices in accordance with the invention can be utilized in microfluidic devices to maximize throughput by decreasing the throughput time for a variety of assays. Embodiments of the invention can significantly improve the throughput of processes involving the screening of large libraries such as combinatorial libraries. Those screening processes can be time consuming due to the aggregation of time requirements for assay of each component in the library. While microfluidic devices reduce the time required for such large screening processes, the time required for assays that have low throughput or non-optimized throughput can also be significantly improved. Embodiments of the methods and devices of the current invention increase throughput by decreasing the amount of time needed to perform mobility shift assays in microfluidic devices.

To decrease the time needed to perform mobility shift assays on a microfluidic device, embodiments of the current invention apply pulsed electric fields through the microchannels of the microfluidic device. The manner in which these pulses are applied, which may be coordinated with the flow of one or more of the molecules being assayed, can be optimized for a specific assay(s), compensating for the specific properties (such as electrophoretic mobility) of the molecules being assayed.

Embodiments of the present invention also optionally include components for controlling fluid flow, generating and controlling pulsed electric fields, reconstituting dried or immobilized samples, controlling temperature, detecting and quantifying molecules, and positioning components or devices (e.g., robotic devices).

In many applications of microfluidic devices, different species are mixed together so that they can interact to form one or more product. Any or all of the reactant species or reaction products may have different electrophoretic mobilities. For example, an enzyme and substrate may be mixed within a microfluidic device to produce a product, and the substrate, product and enzyme may all have different electrophoretic mobilities. When a given electric field is applied across a microfluidic channel by placing electrodes at the end of the channel, a species within the channel will move at a velocity largely determined by their respective electrophoretic mobilities. The electrophoretic mobility of a species is a function of the charge of the species, the size of the species, and the fluid through which the species is moving. So, for example, if all other factors influencing electrophoretic mobility are equal, highly charged molecules will have a greater attraction for an oppositely charged electrode than more modestly charged molecules, making more highly charged molecules travel toward an oppositely charged electrode with a higher velocity. Molecules with differing electrophoretic mobilities can be separated in microfluidic devices, thus making it possible to monitor and characterize interactions between various molecules.

In embodiments of the invention, detection equipment downstream from a reaction site in the microfluidic device can determine the concentration of reactants and products based, in part, on the differing electrophoretic mobilities of these components. For example, if an enzyme and a substrate are mixed at the start of a microchannel, and the enzyme and substrate interact as the mixture flows down the channel, the amount of the product of the interaction appearing downstream from the reaction site as a function of time will depend on factors such as the rate of the reaction, and whether non-rate limiting amounts of reactants (substrate and enzyme) are provided. In addition, the relative concentrations of product, enzyme, and substrate measured downstream of the reaction site as a function of time will depend on the relative electrophoretic mobilities of those three species. For example, if the mobility of the product is substantially lower than the mobility of the substrate, then changes in product and substrate concentrations within the microchannel will appear at the detector at different times.

Embodiments of the invention are able to use differences in electrophoretic mobility to determine reaction rates for many different reactant concentrations in very short periods of time and in very small volumes of fluids. The ability to assess reaction kinetics while the reaction is occurring and while the components are flowing through a microchannel past a detector greatly increases the rate at which such reactions can be assessed. This facilitates accurate high-throughput determination of reaction kinetics, and has a variety of other applications in regard to applications such as drug screening, nucleic acid sequencing, and enzyme kinetics. Embodiments of the invention can be used to examine reactions between two or more components that chemically join (by forming a covalent or non-covalent association) to form a new component or complex. Other reactions that can be examined by embodiments of the invention include reactions in which a reactant is transformed into a product by means of an enzyme, a catalyst, or exposure to electromagnetic radiation. Embodiments of the invention can also be used to examine the spontaneous degradation of a component. In many embodiments, a first component and a second component are mixed together in a channel of a microfluidic device, where the components react to form a product. The product, along with the reactants, can be characterized by pulsed field assays in accordance with the invention.

Mobility Shift Assays

Mobility shift assays, which separate species by means of their differing electrophoretic mobilities, can be used to track and analyze various biochemical reactions. The use of mobility shift assays has been described in the previously cited patent entitled "Apparatus and Methods for Correcting for Variable Velocity in Microfluidic Systems," by Kopf-Sill et al.

Electrophoretic separation processes are often described in terms of flux and velocity. The flux J of a species is equal to the product of the velocity V at which molecules of the species move through a solution and the concentration C of the species in that solution. Flux is typically expressed in units of number of molecules/(cross sectional area·time) or mass/(cross sectional area·time)).

Within a system, such as microfluidic device, the principle of conservation of mass dictates that the total flux of all species (in terms of mass) must be conserved within the system. So, for example, in a three component system, which has a first reactant with a mass concentration (i.e., mass/volume) $C_1$, and a velocity $V_1$, a second reactant with velocity $V_2$ and mass concentration $C_2$, and a product, with velocity $V_p$ and mass concentration $C_p$, the requirement that flux be conserved within the system dictates that the mass flux at a first point w in a microchannel must equal the mass flux at a second point z in the channel as long as no material has entered or left the channel between those two points. In equation form, the conservation of flux is expressed as $V_{1w}C_{1w} + V_{2w}C_{2w} + V_{pw}C_{pw} = V_{1z}C_{1z} + V_{2z}C_{2z} + V_{pz}C_{pz}$. An alternative notation is $[V_1C_1 + V_2C_2 + V_pC_p]_w = [V_1C_1 + V_2C_2 + V_pC_p]_z$. A more general notation that allows for an arbitrarily number of species at the first and second points in the channel is:

$$\sum_{i=1}^{m} ViCi = \sum_{j=1}^{n} VjCj \quad (1)$$

where $C_i$ is the mass concentration (not molar concentration) of the $i^{th}$ species at the first point in the channel, m is the number of species at the first point in the channel, $C_j$ is the mass concentration (not molar concentration) of the $j^{th}$ species at the second point in the channel, and n is the number of species at the second point in the channel. The different species and different number of species occurring at the first and second points in the channel allow for any reactions that may have taken place in the channel. Thus, the sum of the mass concentration times the velocity of each of the species before a reaction is equal to the sum of the mass concentration times the velocity of each of the species after a reaction. In the cases when the reaction yields no net change in the total number of molecules, the molar flux as well as the mass flux is conserved.

When a reaction occurs as fluid flows through a channel in a microfluidic device, and the channel is subjected to an electric field, the various components of the fluid (i.e., the molecular species) typically travel along the length of the channel at different velocities to a downstream position. At one or more downstream positions known as detection points, one or more of the species is detected, typically by means of a label.

At one or more the detection points, the velocities of one or more reactants ($V_{r1}$, $V_{r2}$, $V_{r3}$, etc.) or products ($V_{p1}$, $V_{p2}$, $V_{p3}$, etc.) in the channel are determined by detecting those one or more reactants or products. The velocities of the reactants or products that were not detected can be determined using the conservation of flux equation (equation (1)), or by using the equations that describe how those undetected reactants or products move in an electric field. When an electric field is applied to a channel filled with a fluid, the electric field causes each species in the fluid to move down the channel at a velocity $V_{tot}$, which is equal to the vector sum of the electroosmotic velocity of the fluid $V_{eo}$ and the electrophoretic velocity of the species $V_{ep}$:

$$V_{tot} = V_{eo} + V_{ep} = (\mu_{eo} + \mu_{ep})E \quad (2)$$

In equation (2), $\mu_{eo}$ and $\mu_{ep}$ are the electroosmotic mobility of the buffer and the electrophoretic mobility of the dissolved species, respectively, and E is the applied electric field. The electrophoretic mobility $\mu_{ep}$ is a function of the charge-to-hydrodynamic radius ratio of the species. The hydrodynamic radius of a species depends on the size and shape of the species, and the viscosity of the fluid. The electroosmotic mobility is a function of the surface properties of the channel, and the permittivity and viscosity of the fluid.

Although products of reactions typically change velocity as they are made from, or by, reactants, the velocity change is often considered to be instantaneous because the product reaches its terminal velocity in the system in a very short period of time. Thus, discounting the velocity changes due to the pulsed electric fields, the velocity of a product is essentially constant immediately following formation of the product. Where the velocity changes significantly over time, due to, e.g., a change in the applied pulsed current, or where a change from substrate to product results in a slow acceleration (or deceleration) in the system, an "instantaneous velocity" equal to the change in distance for a selected time can be determined by graphing distance against time and taking the derivative of the resulting function at a particular point in time. There are situations where the electric field strength in a channel varies for reasons other than a change in the electric field being applied to that channel. For example, the electric field strength in a channel could change because of a change in the ionic strength of the fluid in the channel.

Tracking of biochemical reactions in a microfluidic device through a mobility assay (and particularly through use of a pulsed field mobility assay as described herein) allows for the determination of concentrations of the species involved (and their concentration changes over time), the rate of the reaction, and enzyme kinetics of the reaction.

Velocity typically refers to the distance a selected component, or other molecular species travels (l) divided by the time (t) required for the travel. In traditional mobility shift assays, the velocities of the various species are essentially constant as those species travel along the length of a microchannel under a constant electric field in an electrokinetic system. However, as explained below, the present invention applies pulsed electric fields to a microchannel in a microfluidic device. These pulsed fields create a situation where the velocities of the species in the microchannel are not constant.

The detection of results for many biochemical assays in conventional experimental methodology, as well as in microfluidic devices, is oftentimes based upon the use of fluorogenic or chromogenic labels. In such assays the quantum efficiency of a labeling fluorescent moiety or the amount of colored label (chromophore) changes as a result of a reaction, thus allowing for detection and/or characterization of that reaction. However, for certain classes of assays, no fluorogenic or chromogenic labels are available. Assays in which the fluorescence or color a label does not change upon reaction are known as non-fluorogenic and non chromogenic assays respectively.

However, essentially any analysis in which a reactant is converted to a product with a different mobility than the reactant can be analyzed in an appropriately configured microfluidic device through use of a mobility shift assay (especially pulsed field assays as described herein). Such mobility shift assays are velocity-based or velocitogenic assays. One class of reactions that can be analyzed using velocity-based assays in accordance with the invention is enzymatic reactions. A specific class of enzymes is kinases, which are enzymes that recognize specific polypeptide sequences and phosphorylate them. Phosphorylation changes the charge, mass and structure of the polypeptide substrate, so the electrophoretic mobilities of the non-phosphorylated and phosphorylated species are different. As a consequence of this change in mobility, the non-phosphorylated and phosphorylated species move at different rates in an applied electric field (either a traditional steady field or a pulsed field as in the current invention). Therefore, accurate rate determination and quantification of the phosphorylation reaction can be determined through measurement of the velocities and concentrations of the various reactants and products. In other words, a distinct label does not have to be applied to the products to distinguish them from the reactants. It will be appreciated that reactions involving kinases are only one example of reactions that may be analyzed by embodiments of the invention. In other words, while tracking/characterization of kinase reactions through use of the invention is one possible use, many other reactions (both enzymatic and not) are also amenable to use with the current invention.

In conventional mobility shift assays an enzyme (such as a kinase) and a fluorescently-labeled substrate are introduced into a reaction channel continuously by means of a steady vacuum applied to a portion of the microfluidic device downstream of the reaction channel. After flowing through the reaction channel, the reaction products and any remaining reactants flow through a separation channel. Signals from fluorescently labeled species are detected at the end of the separation channel. Signals emanate from both any remaining substrate and product, since the fluorescent label on the substrate remains on the substrate when it is converted to product. When a species that inhibits the reaction is introduced into the reaction channel, the detected signals will reflect the inhibitor's effect on the reaction between enzyme and substrate. The change in detected signals will be determined by the degree of inhibition, and on the spatial separation of the substrate and product signals caused by the differing electrophoretic mobilities of those species. The magnitude of the change in the fluorescent signals indicates the potency of the inhibitor (e.g., percent inhibition), and the spatial separation between the substrate and product signals depends on the electric field strength and the transit time in the separation channel. For a small difference in mobility, either the field strength or the transit time has to increase to achieve acceptable resolution. An increase in transit time causes an increase in diffusion and dispersion, which in turn reduces the assay resolution.

It will be appreciated that the concepts described herein for non-fluorogenic assays are equally applicable for non-fluorescent systems in which the label is other than a fluorophore. So, for example, embodiments of the invention may be applied to systems using colorimetric labels, radioactive labels, mass labels (e.g., such as might be detected by mass spectrometry), or electrochemical labels. It should also be noted, that the terms non-fluorogenic assay and mobility shift assay (regardless of whether the assay involves a constant or pulsed field) are used interchangeably herein. Both of these terms apply to assays based upon the difference in electrophoretic mobility between a product and a reactant. So, for example, both those terms would apply to embodiments of the invention involving a non-chromogenic assay (an assay in which the color or intensity of a label does not change upon reaction), and a non-radiogenic assay (an assay in which the radioactive component of the label is not modified by the reaction). Therefore, for simplicity herein, when fluorogenic assays and non-fluorogenic assays are discussed herein, similar comparisons apply for assays involving radio labels, chromophore labels, pH labels, ionic labels, or other common labels known to one of skill in the art.

Non-fluorogenic assays can be carried out in a microfluidic device in which electroosmotic flow is occurring by periodically injecting reaction mixture into a separation channel in the device within which reactants and products are separated by electrophoresis due to changes in the electrophoretic mobility resulting from the reaction. This type of assay is referred to as a non-continuous assay. Assays employing such periodic injections are described in "Complexity and performance of on-chip biochemical assays" by A. R. Kopf-Sill, T. Nikiforov, L. Bousse, R. Nagel, & J. W. Parce in *Proceedings of Micro-and Nanofabricated Electro-Optical Mechanical Systems for Biomedical and Environmental Applications*, SPIE, Vol. 2978, San Jose, Calif., February 1997, p. 172-179. The length of each periodic injection is typically on the order of from about 0.0001 to 10 minutes, typically about 0.001 to 1 minute, often about 0.1 seconds to 10 second.

Mobility shift assays can also be carried out in microfluidic devices in which electroosmotic flow is occurring by continuously injecting the reaction mixture into a channel. This type of assay is referred to as a continuous assay. In many biochemical reactions, the electrophoretic mobility $\mu_{ep}$ of a reactant molecule changes as a result of the transformation of that reactant into a product by the reaction (e.g. a moiety is added to or cleaved from the reactant during the reaction). Such a change in electrophoretic mobility $\mu_{ep}$, and therefore velocity $V_{tot}$ (see equation (2)), allows for the detection of non-fluorogenic reactions in a continuous flow format.

Determination of concentration of a reaction or assay product $C_p$ through a mobility shift assay in a channel of a microfluidic device is also possible. To determine the concentration of a species, the species is labeled (e.g., with a fluorophore or chromophore) and flowed down a microfluidic channel and past a signal detector. In an exemplary embodiment, the labeled species is a labeled first reactant having a velocity $V_r$. This labeled first reactant produces a signal, such as a fluorescent signal, detectable by the detector. The labeled first reactant is converted to a labeled reaction product, the product having a velocity $V_p$. In the typical case, $V_r$ does not equal $V_p$, meaning that the signals from the labeled first reactant and the labeled product will not be detected by the detector at the same time because the reactant and product were physically separated as they traveled down the microfluidic channel because of their differing velocities. Accordingly, the two signals can be separately detected. The relative sizes of the signals produced by the reactant and the product provide an indication of the relative concentrations of those species. In some embodiments, the concentrations of reactant, as indicated by the size of the signal produced by reactant, in the presence and in the absence of the reaction of interest can be compared. An absence of reaction can be created by, for example, not adding another reactant that is required to initiate the reaction. The signal pattern (i.e., signal as a function of time) produced in the absence of reaction can serve as a baseline to which signals produced in the presence of reaction can be compared.

In many embodiments of non-fluorogenic assays, a labeled reactant molecule is converted by a reaction to a labeled product molecule by treating the labeled reactant molecule with any physical component or force that brings about the conversion. Such components or forces include light, heat, electrical charge, a polymerization agent, a catalyst, and a binding molecule. In some embodiments, the label moiety on the labeled reactant and labeled product are identical. In alternative embodiments, the label on the labeled reactant is modified so that a different label is present on the labeled product. Even with such a modification, however, the output (e.g., light of a particular wavelength) of the label typically does not change in a non-fluorogenic assay. Of course, where the label does change, the mobility shift assays can also be applied, as the velocity will typically concomitantly change.

In a microfluidic device in which an electric field is applied along the length of a microchannel, charged species such as analytes, solvent molecules, reactants and products move along the microchannel by means of the electrokinetic forces of electroosmosis and electrophoresis. The net mobility of each species is determined by the vectorial sum of the electroosmotic and electrophoretic mobilities, the latter of which is a function of the hydrodynamic radius-to-charge ratio of each species. As previously discussed, the hydrodynamic radius-to-charge is proportional to the velocity in a flowing system. In various embodiments, the fluid flow in the system may result from the application of electrokinetic forces or pressure forces. During a chemical or biological reaction such as ligand-receptor binding or antibody-antigen binding, the reactants in general have different electrophoretic mobilities than the products. The differences in mobilities are exploited in non-fluorogenic assays in accordance with the invention in which the ability to separately detect reactants and products is not dependent on the production or quenching of fluorescence as a consequence of the reaction. Instead, the mobility difference is used to separate the "reactant hole", the change in signal from the baseline that reflects the decrease in reactant concentration caused by the consumption of the labeled reactant in the reaction, from the "product peak", the change in signal from the baseline reflecting the increase in product concentration caused by production of labeled product in the reaction. The difference between the baseline and the signal pattern produced as a result of the reaction of interest taking place under continuous flow conditions provides a signature from which quantitative information on the reaction kinetics can be extracted.

Figure 1B:
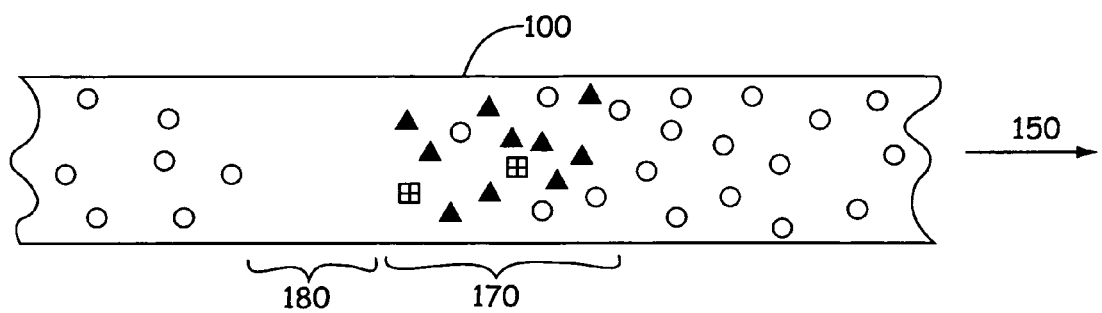

FIG. 1 illustrates the basic concept of a continuous flow mobility shift assay by applying the concept to a binding reaction A+B→P, where A is a fluorescently labeled reactant, B is an unlabeled reactant, and P is a product. In FIG. 1, the fluorescently-labeled reactant molecules are denoted by circles, the unlabeled reactant molecules are denoted by squares, and the reaction product molecules are denoted by solid triangles. Note that the reaction product molecules formed by the binding reaction will also be labeled since the product molecules will comprise the label from the labeled reactant. In the exemplary embodiment of FIG. 1, the binding reaction is fast and has a high association constant $K_a$, where $K_a=[P]/[A][B]$ (the brackets denoting concentrations). The labeled reactant molecules (circles) are introduced into the main channel 100 at a constant concentration. Before the binding reaction occurs, the total concentration of fluorescently labeled molecules in the channel 100 will be equal to that constant concentration of labeled reactant molecules. This before-reaction total concentration of fluorescently labeled molecules will provide a baseline signal at the detector. In this embodiment, the labeled reactant is assumed to have a lower electrophoretic mobility than the product, so the labeled reactant moves more slowly down the channel 100 than the product. As indicated by the arrows 150, the direction of flow in channel 100 is from left to right.

To initiate the binding reaction, a short pulse or plug 160 of unlabeled reactant molecules (squares) is injected into the main channel 100 from a side channel (not shown). Panel A of FIG. 1 shows the situation at the instant the plug 160 of unlabeled reactant molecules (squares) is injected into the main channel 100. After the injection, the unlabeled reactant molecules (squares) will bind to the labeled reactant molecules (circles), converting the labeled reactant molecules to relatively fast moving product molecules (triangles). For purposes of simplifying the example, the binding reaction is considered to occur instantaneously. Panel B of FIG. 1 illustrates the situation some time after the binding reaction has occurred. In the time after the reaction, the faster moving product molecules (triangles) have moved down the channel 100 faster than the labeled reactant molecules (circles), thus giving rise to a portion 170 of the fluid in the microchannel 100 containing a higher local total concentration of fluorescent species (i.e., the sum of the fluorescence from the baseline concentration of labeled reactants and the additional fluorescence of labeled products). Accordingly, this fluid portion 170 will produce a fluorescent signal higher than the baseline signal. The portion 180 of the fluid in the microchannel where the binding reaction took place will have a lower concentration of labeled reactant molecules (circles) due to the depletion of those molecules by the reaction. Accordingly, that portion 180 of the fluid will have a lower total concentration of fluorescent species that will produce a fluorescent signal lower than the baseline signal.

Quantitatively, it is important to recognize that the portion 170 of the fluid containing the product occupies a larger volume in the channel than the depleted portion 180 of the fluid reactant zone due to the higher velocity of the product. Consequently, the maximum increase in concentration of product in the channel will be less than the maximum decrease in concentration of the labeled reactant since both the total increase and decrease consist of the same number of product and reactant molecules respectively. Interestingly, when the fluorescence seen by a stationary detector, which the fluid in channel 100 flows past, is plotted against time, the widths of the peak (caused by the product) and valley (caused by depletion) are the same because the spatially wider product peak, which has been increased by a factor equal to the ratio of product velocity $V_p$ to reactant velocity $V_r$, moves past the detector faster by the same factor of $V_p/V_r$. If the decrease in molecular concentration of the product $C_r$ in fluid region 180 is known, the velocities $V_r$ and $V_p$ are known, the molecular concentration of the product $C_p$ in fluid region 170 can be calculated as $C_p=C_r(V_r/V_p)$, since in the exemplary reaction of this embodiment the number of molecules of reactant consumed by the reaction is equal to the number of molecules of product produced by the reaction.

When a label detector (e.g., a photomultiplier tube or a photo diode) is placed downstream of the injection point, whether the plug of faster moving product will be partially or totally separated from the slower moving depletion hole when the plug and hole reach the detector will depend on the distance between the injection and detection points, the width of the injection plug, and the relative velocities of the labeled reactant and product. In the case of partial separation, a plot of the detector signal as a function of time will show a peak followed by a plateau region and a valley. The ratio of the magnitude of the peak to valley is $C_p/C_r$, which, by algebraic manipulation, is equal to $V_r/V_p$. The plateau region is lower in fluorescence than the background level. The ratio of the magnitude of the plateau region to the valley is $1-(C_p/C_r)$ or $1-(V_r/V_p)$. In the case of total separation, the signal shows a peak and a valley separated by the baseline fluorescence level instead of the plateau region.

As in conventional capillary electrophoresis, the resolution of the separation is directly proportional to the electric field strength and the transit time in the separation channel. In some situations, however, the length of time needed to obtain adequate resolution can be deleterious to throughput. For a small shift in mobility, either the field strength or the transit time has to increase in order to achieve acceptable resolution. For example, if the reactant and product only differ by a small amount in their mobility, a relatively long transit time may be required to achieve acceptable resolution. The transit time can be increased by increasing the distance from where the reaction occurred to the detector. An increase in transit time, however, causes an increase in diffusion and dispersion that reduce the gains in resolution. Additionally, in the analysis of fast off-rate binding reactions, it is desired to measure the reaction as soon as possible (i.e., as soon after the reaction occurs as possible). Therefore, the long transit time that may be needed to adequately separate the reactants and products would distort the results of the analysis of the reaction.

Pulsed Field Mobility Shift Assays

Mobility shift assays that involve the application of pulsed electric fields can separate species much more rapidly than can mobility shift assays that involve the application of constant electric fields. Embodiments of the present invention involve the application of a pulsed electric field that induces a temporal change in the electrophoretic velocity of the species in a sample as a fluid comprising the sample flows through a microchannel. In exemplary embodiments, the flow of the fluid may result from electroosmosis or the application of pressure (e.g., a positive pressure or a vacuum). A detector located in a portion of the microchannel subjected to a pulsed electric field can measure the time-dependent perturbations of the concentrations of species, from which perturbations of the velocities of species can be derived through application of the principle of mass flux conservation. The temporal change in concentration of species can also be related to the electrophoretic mobilities of the species. Embodiments of the invention can determine the extent of a reaction that involves a fluorescently labeled reactant and a fluorescently labeled product that have different electrophoretic mobilities, even when the fluorescent labels on the reactant and product are identical. The pulsed field assays of the invention have a wide range of applications, and are especially advantageous when applied to high throughput processes. Embodiments of the invention may also include continuous flow assays, which in some cases have higher throughput than assays requiring the additional step of sample injection. Since embodiments of the current invention take less time than existing assays, application of the invention may help reduce problems in existing assays that stem from the dispersion of sample bands.

In embodiments of the invention, an electric field being applied to a microchannel is pulsed from a first value $E_1$ to a second value $E_2$. In various embodiments, either the first or second value can comprise a zero value, so the electric field is pulsed from "off" to "on" or vice versa. In other embodiments, $E_1$ and $E_2$ both have non-zero values, so the electric field is pulsed from a non-zero value to another non-zero value. Such non-zero pulses may be separated by periods in which no electric field is applied. In some embodiments, the pulsed electric field results in a voltage profile comprising pulses of opposite polarity that are symmetric about a zero value (e.g., $E_1$ produces a negative voltage while $E_2$ produces a positive voltage of the same magnitude). If the time durations of the symmetric pulses of opposite polarity are equal, then the fluid being subjected to the pulsed field will have no net electrokinetic motion induced by the application of the pulsed field. In other embodiments, zero net electrokinetic motion is achieved by applying a pulsed electric field in such a way that the field produces voltage pulses of opposite polarity where the product of voltage pulse duration and pulse magnitude for each of the opposite polarity pulses is equal.

A variety of electric field pulse patterns may be applied in various embodiments of the invention. For example, in some embodiments the time periods of the electric field pulses and the time periods between pulses are not equal. In those embodiments a pulse may comprise a shorter or longer length of time than the period between pulses. In other embodiments, the time periods of the pulses and the pause between pulses are of equal length. In still other embodiments, the time period of pulses or pauses between pulses may vary between successive pulses or sets of pulses (e.g., pairs of symmetric pulses of opposite polarity). Similarly, the magnitude of pulses may vary between successive pulses or sets of pulses.

A variety of different relationships between the electric field pulse patterns applied to a microchannel and the manner in which samples are introduced into that microchannel are compatible with the invention. For example, the electric field may be pulsed at frequencies higher or lower than the sample injection rate. In other words, the number of electric field pulses per unit time applied to a microchannel can exceed or be less than the number of injections of sample per unit time into that microchannel. It is also possible to apply one pulse in electric field for each injection of sample.

Figure 2:
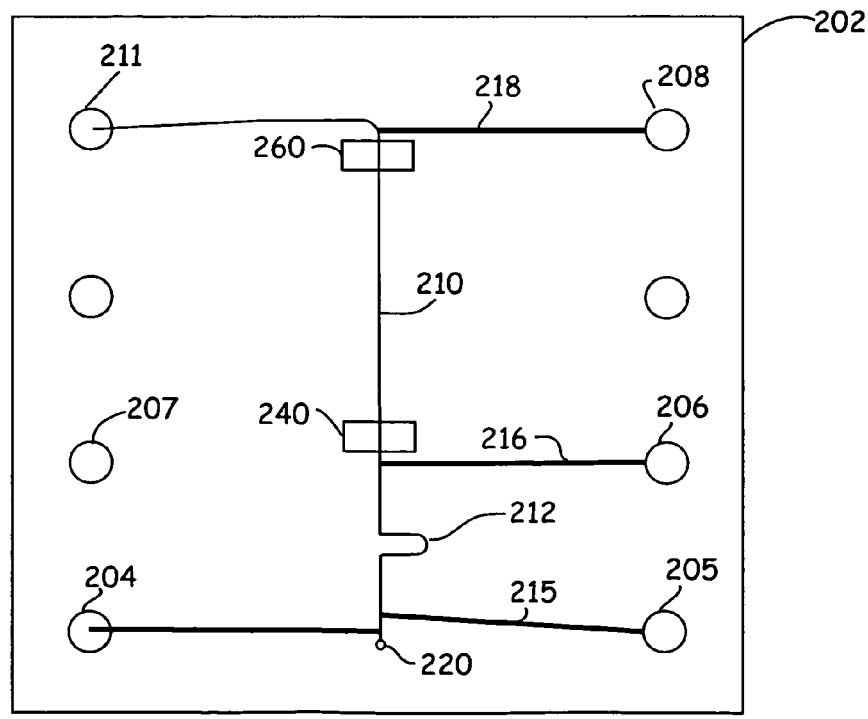
FIG. 2 schematically represents an exemplary microfluidic device in accordance with the invention that is capable of performing a pulsed field assay.

A schematic representation of a microfluidic device in accordance with the invention is shown in FIG. 2. A microfluidic device is a device in which fluid flows that has a feature, such as a chamber, channel, or reservoir with a cross-sectional dimension (e.g., depth, width, length, or diameter) of about 0.1 µm to about 500 µm. Exemplary microfluidic devices are described in U.S. Pat. No. 5,942,443 entitled "High Throughput Screening Assay Systems in Microscale Fluidic Devices", which issued Aug. 24, 1999. The microfluidic device 202 in FIG. 2 comprises a separation channel 210 in which species can be separated by means of differences in their respective electrophoretic mobilities. A pulsed electric field can be applied to the separation channel 210 by applying voltages to electrodes placed in reservoirs 206 and 208. The separation channel 210 is intersected by at least one other microscale channel (e.g., channel 216) disposed within the body of the device. Such intersecting channels are used to transport materials into or out of the separation channel 210. So, in the embodiment of FIG. 2, reservoirs 204 and 205 could contain the various reactants whose interactions are to be assayed. In other embodiments, only a sub-portion or sub-region of a separation channel is subjected to a pulsed field.

Although the embodiment of FIG. 2 comprises a single separation channel 210, other embodiments may have two or more additional separation channels are disposed within the microfluidic device 202. For example, in a microfluidic device with multiple separation channels, parallel pulsed field mobility shift assays could be carried out in different separation channels so that the effects of a particular enzyme has on a number of different substrates could be simultaneously evaluated. In some embodiments, a single microfluidic device could include from about 1 to about 100 or more separation channels specifically configured to perform pulsed field assays in accordance with the invention.

The materials transported into or out of separation channel 210, such as reactant, products, buffers or reagents, may also be transported out of or into reservoirs fluidly connected to the separation channel 210 by other microscale channels. These reservoirs may contain the materials required to carry out assays in accordance with the invention, as well as to any other operations that are carried out on the microfluidic device 202. Examples of different reservoirs that could be employed in embodiments of the invention are a reservoir containing a dilution buffer to be added upstream from the source of a reagent to dilute the reagent, and a reservoir that functions as waste well to store samples after a reaction or assay has been completed. The removal of the completed samples provides space in the channels to load and incubate other samples. In this fashion, the devices of the invention can be used in a high throughput manner. The high throughput can be achieved by continuously loading, processing, and unloading samples into and out of the microchannels of the device. Increased throughput, in fact, is one of the major benefits of the current invention. Because reaction products need not be flowed for such a long period of time (as in traditional electrophoretic separation assays), more samples can be loaded in the same period of time.

In other embodiments, materials may be introduced into the microfluidic device 202 from sources outside the device, as opposed to sources such as reservoirs within the device. Materials outside the device can be transported to the device by means of a "capillary element" or other similar pipettor element. The capillary element can be temporarily or permanently coupled to a source of fluidic material. In the embodiment of FIG. 2, a capillary interfaces with the microfluidic device 202 at intersection 220. Capillary elements can transport materials from such external sources as microwell plates, solid substrates comprising lyophilized components, or reservoirs in a microfluidic device. The use of capillary elements is described in U.S. Pat. No. 5,880,071 entitled "Electropipettor and Compensation Means for Electrophoretic Bias" by J. Wallace Parce et al., which issued Mar. 9, 1999.

In embodiments of the present invention, a dilution buffer is typically added into the separation channel upstream of an optional shunt channel, so that the increase in flow rate due to the addition of buffer material downstream of its entry point may be counteracted by the reduction in pressure due to the shunt channel. Reagent materials, on the other hand, are typically added downstream of an optional shunt channel so that they are added after the downstream flow rate in the main channel has been reduced so that smaller quantities of reagent are added.

In general, microfluidic devices are planar in structure and are constructed from an aggregation of planar substrate layers wherein features such as microchannels are formed at the interface of the various substrate layers. In some embodiments, the microchannels are fabricated by etching, embossing, molding, ablating or otherwise fabricating into a surface of a first substrate grooves. A second substrate layer is subsequently overlaid on the first substrate layer and bonded to it in order to cover the grooves in the first layer, thus creating sealed features within the interior portion of the device. Microfluidic devices in accordance with the invention can take a variety of forms, and do not need to have a layered planar structure. For example, microfluidic devices in accordance with the invention may include aggregations of various components such as capillary tubes and individual chambers that are pieced together to provide the integrated elements of the complete device.

Manufacturing of these microscale elements into the surface of the substrates can be carried out through any number of microfabrication techniques that are well known in the art. For example, lithographic techniques are optionally employed in fabricating, e.g., glass, quartz or silicon substrates, using methods well known in the semiconductor manufacturing industries such as photolithographic etching, plasma etching or wet chemical etching. Alternatively, micromachining methods such as laser drilling, micromilling and the like are optionally employed. Similarly, for polymeric substrates, well known manufacturing techniques may also be used. These techniques include injection molding or stamp molding methods wherein large numbers of substrates are optionally produced using, e.g., rolling stamps to produce large sheets of microscale substrates, or polymer microcasting techniques where the substrate is polymerized within a micromachined mold. Furthermore, various combinations of such techniques are optionally combined to produce the microelements present in the current invention.

The substrates used to construct the microfluidic devices of the invention are typically fabricated from any number of different materials, depending upon such factors as the nature of the samples to be assayed and the specific reactions and/or interactions being assayed. For some applications, the substrate can optionally comprise a solid non-porous material. For example, the substrate layers can be composed of silica-based materials (such as glass, quartz, silicon, fused silica, or the like), polymeric materials or polymer coatings on materials (such as polymethylmethacrylate, polycarbonate, polytetrafluoroethylene, polyvinylchloride, polydimethylsiloxane, polysulfone, polystyrene, polymethylpentene, polypropylene, polyethylene, polyvinylidine fluoride, acrylonitrile-butadiene-styrene copolymer, parylene or the like), ceramic materials, or metallic materials (e.g., wherein the metal materials are coated with an electrical insulation layer such as a metal oxide).

The surface of a substrate layer may be of the same material as the non-surface areas of the substrate or, alternatively, the surface may comprise a coating on the substrate base. For example, a surface may be coated in order to reduce or prevent electroosmotic flow in the separation channel. Furthermore, if the surface is coated, the coating optionally can cover either the entire substrate base or can cover select portions of the substrate base (e.g., only the separation channel is so coated). For example, in the case of glass substrates, the surface of the glass of the base substrate may be treated to provide surface properties that are compatible and/or beneficial to one or more sample or reagent being used. Such treatments include derivatization of the glass surface, e.g., through silanization or the like, or through coating of the surface using, e.g., a thin layer of other material such as a polymeric or metallic material. Derivatization using silane chemistry is well known to those of skill in the art and can be readily employed to add, e.g., amine, aldehyde, or other functional groups to the surface of the glass substrate, depending upon the desired surface properties. Further, in the case of metal substrates, metals that are not easily corroded under potentially high salt conditions, applied electric fields, and the like are optionally preferred.

One major advantage of the methods and devices of the present invention is that pulsed field assays enhance the throughput rate through the separation channel (and hence, the throughput through the microfluidic device). A detector (e.g., to read the fluorescence levels indicating electrophoretic separation of species) can thus be located much closer to the start of the separation channel instead of near the end (e.g., compare detector 260 and detector 240 in FIG. 2).

With the methods and devices of the present invention, the detector no longer has to wait until the species are electrophoretically separated in the regular steady state field. Instead, as in FIG. 2, the detector (again, e.g., detector 240) can be right near the beginning of the separation channel.

In an exemplary application of the device 202 in FIG. 2 to a pulsed field assay in accordance with the invention, channel 210 is fluidly coupled to channel region 212, which is connected to capillary element 220 that can access samples stored outside of the device in a microwell plate or the like. For example, capillary element 220 can access a microwell plate (or even numerous microwell plates accessed via a robotic armature) that contains a number of compounds to be screened within the microfluidic device. Within the reaction channel region, 212, reactants such as an enzyme and a putative substrate, or a receptor and a putative ligand, interact.

The fluidic material (or more typically, a mixture of fluidic materials) drawn through capillary element 220 can be mixed with a buffer in order to, e.g., dilute the sample to a proper concentration for the necessary assays/reactions to occur and/or to help dilute unwanted sample storage materials such as DMSO. To accomplish such, a quantity of buffer can be flowed from a buffer reservoir (not shown) and mixed with the contents of the main channel. Alternatively, additional fluidic materials in place of, or in addition to, buffers are optionally flowed into the channel from, e.g., other reservoir(s).

In the embodiment of FIG. 2, the fluidic material drawn through the capillary is joined by materials flowing from reservoirs 204 and 205. In some embodiments, the material drawn through the capillary is a compound being screened as a potential inhibitor to a reaction between the materials introduced from reservoirs 204 and 205. Accordingly, the material from the two reservoirs could be enzymes, substrates, receptors, ligands, nucleic acids, antibodies, antigens, or other reaction system constituents amenable to be assayed through a non-fluorogenic pulsed field mobility shift assay. The mixture of the reactants from the capillary and the reservoirs is flowed into reaction channel region 212. In reaction channel region 212 the fluidic materials undergo their putative interaction. Reaction channel region 212 therefore has the proper conditions for such reaction to take place, such as the proper temperature, pH, and osmolality.

Flow of materials through reaction region 212 can be by any type or combination of types of flow such as electrokinetic or pressure based. In many embodiments pressure based flow is used.

The reaction components next travel into separation channel region 210. Voltage pulses between an electrode in well/reservoir 206 and one in reservoir 208 in FIG. 2, drive the reactants, molecular species through the separation channel region. As explained previously, pressure driven flow can be used in the main separation channel in conjunction with the electrokinetic flow resulting from the pulsed electric field to move materials along and also to help optimize sensitivity of the pulsed field assay.

The pulsed electric fields used to electrophoretically separate constituents in channel region 210 can be optionally modified in duration (e.g., the time on and the time off can be modified, see, above) as well as in intensity (e.g., the voltage level is optionally controllable, see, above). It should be noted that detector 240 is placed at the beginning of the separation channel region in FIG. 2 (i.e., close to the reaction region). This again illustrates a major advantage of the current methods and devices. Because of the pulsed fields of the present invention, the detector can be placed closer to the reaction channel region instead of at the end of the separation channel region (e.g., as with detector 260 in FIG. 2).

The above example, illustrates that the methods and devices of the current invention (i.e., pulsed field electrophoretic separation of different components) are easily adaptable to many different experimental situations and can be adapted to many different uses which may be ancillary and/or additional to other uses of the device.

The pulsing of the voltage (e.g., turning on and off of the voltage) applied to the electrodes immersed in reservoirs 206 and 208 creates a pulsed electric field through the separation microchannel 210 in FIG. 2. The pulsed field will cause a fluorescently (or otherwise labeled) reactant and/or product to have an oscillatory fluorescent signal at detector 240 with the same frequency as the applied pulsed field. This will be true if the labeled molecules in question are electrophoretically active and/or if the microchannel supports electroosmotic flow.

Such pulsing is done at a quicker rate than the rate of intermittent injections of, e.g., substrate into the main reaction channel (i.e., injection from well 205 into reaction channel 212). In other embodiments, different ratios of pulse to injection will apply. In some contexts, e.g., if the system being assayed is very stable and the interval between sample injection and arrival of the peak of the sample concentration at a detector is known, then optionally only one pulse per sample injection would be needed. In embodiments wherein the pulse is from zero to a set value (e.g., as opposed to situations where the pulse goes from one non-zero value to another non-zero value), an optimum length of time during which the field is on (i.e. pulsed) will optionally exist. However, in embodiments wherein the system is not entirely predictable, or in situations wherein it is desirous to collect more data, e.g., to improve signal/noise, more than one pulse is optionally applied for each sample injection. Optionally, as pulse durations become shorter, the amplitude-change in the signal during the pulses gets small, thus setting a guideline to the upper frequency of pulsing in some embodiments.

In some embodiments, the intermittent injection of a sample is done for a period of time that is at least as long as one complete pulse of the electric field/voltage. In situations where two or more samples (e.g., samples of an enzyme and samples of a substrate) are injected intermittently, the interjections typically overlap each other either partially or completely. Of course, in this non-limiting example, instead of substrate, a reaction enhancer, a reaction inhibitor, or a competitive substrate could be the molecule being intermittently injected into the channel 212. In various embodiments, the values of E can range from less than 10 V/cm to up to about 1,000 V/cm or more, from less than 100 V/cm to up to about 500 V/cm or more, from less than 250 V/cm to up to about 300 V/cm or more.

Figure 3:
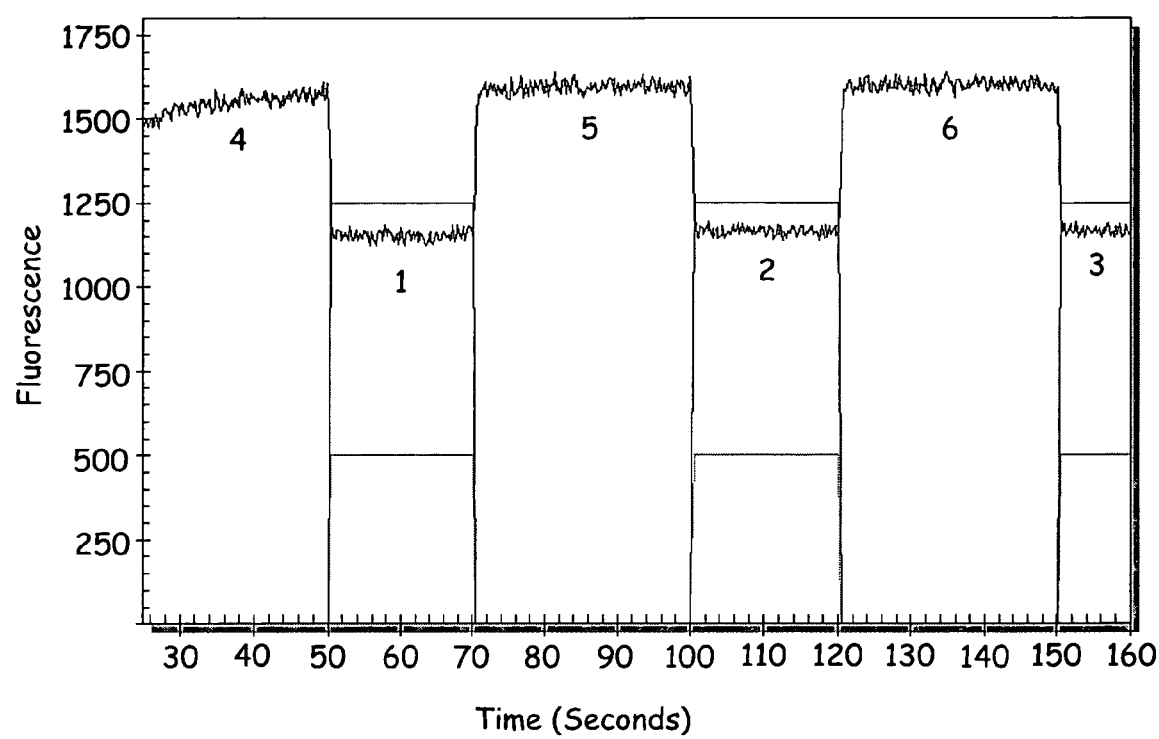
FIG. 3 is a representation of fluorescein fluorescence intensity in a pulsed electric field.

A simple example of the application of a pulsed electric field to a channel in a microfluidic device is illustrated in FIG. 3. FIG. 3 shows a measured level of fluorescence from fluorescein (an electrophoretically active molecule) continuously flowed via a pressure driven flow in a pulsed electric field (with electroosmosis suppressed in the microchannel). The electric field is pulsed between an "on" (i.e. a non-zero electric field is applied) and an "off" (i.e. no electric field is applied) state. As can be seen in FIG. 3, when the pulsed field is 'on' (i.e., points 1, 2, and 3), the intensity of fluorescein fluorescence (and hence its concentration) is lower than when the pulsed field is 'off' (i.e., points 4, 5, and 6) where the level of fluorescence is higher.

The results in FIG. 3 can be explained by the previously discussed conservation of flux equations. Since the amount of fluorescein flowing through the channel remains the same, regardless of whether the pulsed field is "on" or "off", the mass flux, J, of the fluorescein will be constant. In the absence of an electric field, i.e., when the pulsed field is off, the velocity of the fluorescein in FIG. 3 flowing in the microchannel is $V_p$, which the velocity resulting from the application of the pressure. When the electric field is applied, however, the fluorescein will have an additional velocity component from electrophoresis $V_{ep}$. Accordingly, the conservation of mass flux equation dictates that the concentration of the fluorescein at the detection point when the electric field is on, $C_{on}$, will be related to the concentration of the fluorescein at the detection point when the electric field is off, $C_{off}$, by the relation $$J = C_{on}(V_p + V_{ep}) = C_{off} V_p. \qquad (3)$$

Solving for $C_{on}$ gives the relation $C_{on} = C_{off}(V_p/(V_p + V_{ep}))$. When, as in this embodiment, the velocities produced by the pressure and electrophoretic forces are in the same direction, the velocity $V_p$ will be less than the velocity $V_p + V_{ep}$. Thus, as is shown in FIG. 3, the measured value of $C_{on}$ will be lower than the measured value of $C_{off}$ by a factor of $V_p/(V_p + V_{ep})$.

Electroosmotic flow was suppressed in the embodiment of FIG. 3. In general, however, when an electric field is applied to a channel, which occurs during the "on" portion of a pulsed field comprising "on" and "off" states, the velocity of species in the channel will have two additional velocity components: one from electrophoresis ($V_{ep}$) and one from electroosmosis ($V_{eo}$). Therefore, on a time scale short enough so that there is no significant change in the composition of the fluid due to chemical reactions, the mass flux of a species across a cross section of the separation channel when the pulsed electric field is off ($J_0$) and when the pulsed field is on ($J_1$) must be conserved. Since the principle of conservation of mass flux dictates that $J_0$ must equal $J_1$, the concentrations and velocities of the species in the on and off states are related by $$J_0 = C_0 V_0 = J_1 = C_1 V_1, \qquad (4)$$

where $C_1$ is the concentration of species in when the pulsed field is on, and $C_0$ is the concentration of the species when the pulsed field is off. Expressing the velocities in the two states in terms of their component velocities gives, $$\frac{C_0}{C_1} = \frac{V_1}{V_0} = \frac{(V_p + V_{ep} + V_{eo})}{V_p}. \qquad (5)$$

When the electric field is off, the pressure driving force produces the only velocity component. When the electric field is on there are additional electrophoretic and electroosmotic velocity components.

It is useful to define a net electrokinetic velocity $V_{ek}$, which is equal to the sum of the electrophoretic and electroosmotic velocity components ($V_{ep} + V_{eo}$). If the net electrokinetic velocity $V_{ek}$ is in same direction as pressure driven velocity $V_p$, then $C_1$ will always be lower than $C_0$. This was the case in the embodiment of FIG. 3. In FIG. 3, when the pulsed field was on (i.e., in regions 1, 2, and 3) the concentration $C_1$ was lower than the concentration $C_0$ when the field was off (i.e., regions/times 4, 5, and 6).

Additionally, both electrokinetic velocities (i.e., $V_{ep}$ and $V_{eo}$) are directly proportional to the applied electric field, E, by their respective mobilities $\mu_{ep}$ and $\mu_{eo}$. Thus, if we define a net electrokinetic mobility $\mu_{ek}$, which is equal to ($\mu_{ep} + \mu_{eo}$), we obtain the relation $$V_{ek} = \mu_{ek} E. \qquad (6)$$

Inserting this expression for $V_{ek}$ into equation (5) and solving for $\mu_{ek}$ gives the relation $$\mu_{ek} = V_p \left( \frac{\frac{C_0}{C_1} - 1}{E} \right). \qquad (7)$$

It should be noted that in the absence of electroosmosis (e.g., as when the wall of a microchannel is specifically coated to prevent electroosmosis, see below), $\mu_{ek}$ reduces to the electrophoretic mobility of the species $\mu_{ep}$.

Figure 4:
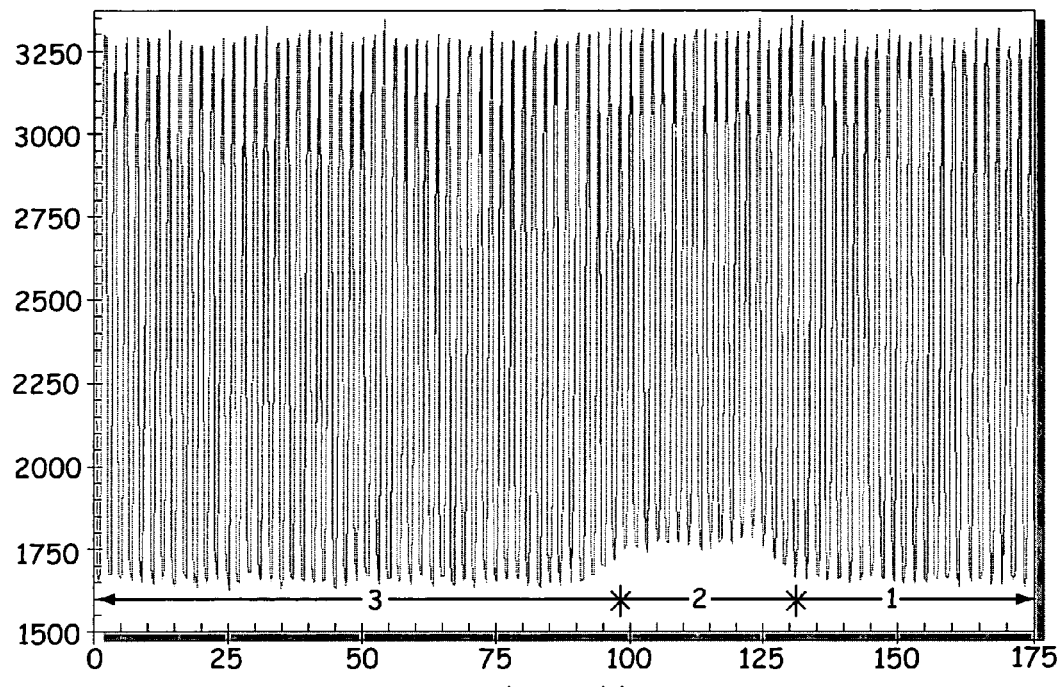
FIG. 4 is a representation of fluorescence intensity of 2 peptides in a pulsed electric field.

While FIG. 3 illustrates the concentration and velocity changes of a single species in a pulsed electric field, pulsed electric field mobility shift assays are typically used to track changes in concentration and velocity of multiple species in a microchannel. These multiple species could be, for example, the species involved in a kinase reaction or a binding reaction. Therefore two species or more are usually assayed. The results from an embodiment where both a fluorescent reactant and a fluorescent product are electrophoretically active is shown in FIG. 4. In FIG. 4, two peptides with different electrophoretic mobilities were drawn into a separation channel and flowed under the pulsed field methods of the present invention. In the separation channel of this embodiment, electroosmosis was suppressed. The pulsed electric field comprised an on state in which an electric field was applied to the channel, and an off state when no electric field was applied. The rate of the pulsed field, i.e., how quickly the electric field was pulsed on and off, was one second on and one second off. The first peptide comprised a polypeptide with six amino acids units and a net charge of −2. Region 1 of FIG. 4 shows the detected fluorescence when only this peptide was present in the separation channel. Next, a nine amino acid polypeptide with a net −2 charge was flowed into the separation channel for 30 seconds. The resulting fluorescence is shown in region 2 of FIG. 4. Finally, the separation channel was again filled with the original six amino acid peptide. The resulting fluorescence is shown in region 3 of FIG. 4. The difference in fluorescence intensities between the six amino acid peptide and the nine amino acid peptide results from the difference in the electrophoretic mobilities of those molecules. Thus, the results shown in FIG. 4 indicate that changes in the electrophoretic mobility of a molecule, as might occur when the molecule is transformed in a reaction or binds to another molecule, can be detected by methods in accordance with the invention.

An additional benefit of using a mobility shift assay employing a pulsed electric field, as opposed to a convention mobility shift assay employing a constant electric field, is that the pulsed field assay can better analyze binding reactions that have a fast "off-rate". In a fast off-rate binding reaction, the binding reaction between the species is rapid and reversible. If the time required to perform a conventional mobility shift assay is long enough, the continuous application of the required electric field might separate the bound and unbound species. Separating those species would affect the reaction equilibrium, distorting the results of the assay. This could occur, for example, when assaying a binding reaction between a receptor and a ligand. For instance, for a binding reaction with an equilibrium association binding constant ($K_{eq}$) of $10^6$ M and an on-rate ($k_{on}$) of $10^7$ to $10^8$ $M^{-1}s^{-1}$, the off rate is on the order of 1 to 10 $s^{-1}$. In such a case, a 1-second pulse should not perturb the equilibrium significantly, while a 20-second separation time, which is commonly required for traditional mobility shift assays, would. Moreover, the signal in the pulsed field method is self-calibrating since the concentration ratio, ($C_0/C_1$), will normalize out effects such as pipetting error and fluorescence quenching due to reaction.

Additionally, the methods/devices of the present invention are optionally calibrated/modified in order to optimize the sensitivity of the pulsed field assay. To illustrate the optimization of a pulsed field assay, a pulsed field assay involving two detectable species, species a and species b, will be optimized. In various embodiments, the two species could be a similarly labeled reactant and product respectively. In order to optimize the exemplary pulsed field assay, the value of $\Delta C_1/C_0$ is maximized, wherein $\Delta C_1$ equals the difference in concentration of the two species when the pulsed field is on and $C_0$ equals the concentration of one of the species when the pulsed field is off. Similarly, in embodiments where the pulsed electric field alternates between two non-zero electric fields, $\Delta C_1$ would be the difference in concentration between the species when one of the two non-zero electric fields is applied, while $C_0$ would be the concentration of one of the species when the other field is applied. To maximize $\Delta C_1/C_0$, the magnitude of the electric field E in the on state, the pressure induced velocity $V_p$, or the electrokinetic mobilities of the two species ($\mu_a$ and $\mu_b$) can be manipulated.

For example, if two species are put through the exemplary pulsed field assay, the conservation of mass flux equation for species 'a' would be $$\frac{C_{1a}}{C_{0a}} = \frac{V_p}{V_p + \mu_a E}, \quad (8)$$

while the corresponding equation for species 'b' would be $$\frac{C_{1b}}{C_{0b}} = \frac{V_p}{V_p + \mu_b E}. \quad (9)$$

The overall sensitivity of the process can be expressed as $$\frac{\Delta C_1}{C_0} = \frac{C_{1a}}{C_{0a}} - \frac{C_{1b}}{C_{0b}} = V_p\left(\frac{1}{V_p + \mu_a E} - \frac{1}{V_p + \mu_b E}\right). \quad (10)$$

Equation (10) can be rearranged to give $$\frac{\Delta C_1}{C_0} = \frac{E}{V_p} \frac{(\mu_b - \mu_a)}{\left(1 + \frac{\mu_a E}{V_p}\right)\left(1 + \frac{\mu_b E}{V_p}\right)}. \quad (11)$$

Therefore, the parameters $V_p$, E and ($\mu_b - \mu_a$) can be manipulated to maximize $\Delta C_1/C_0$, thus maximizing the overall sensitivity of the pulsed field assay. Equation (11) can be rewritten as $$\frac{\Delta C_1}{C_0} = (\mu_b - \mu_a)EV_p\left(\frac{1}{(V_p + \mu_a E)(V_p + \mu_b E)}\right). \quad (12)$$

Differentiating $\Delta C_1/C_0$, with respect to the experimentally controllable variable $V_p$ (i.e., the component of species velocity produced by pressure) gives $$\frac{\partial\left(\frac{\Delta C_1}{C_0}\right)}{\partial V_p} = (\mu_b - \mu_a)E\left\{\frac{1}{(V_p + \mu_a E)(V_p + \mu_b E)} + \frac{-V_p}{(V_p + \mu_b E)(V_p + \mu_a E)^2} + \frac{-V_p}{(V_p + \mu_a E)(V_p + \mu_b E)^2}\right\} \quad (13)$$

To maximize $\Delta C_1/C_0$ with respect to $V_p$, we set $$\frac{\partial\left(\frac{\Delta C_1}{C_0}\right)}{\partial V_p} = 0. \quad (14)$$

Combining equations (13) and (14), and simplifying the result gives $$1 - \frac{V_p}{V_p + \mu_a E} - \frac{V_p}{V_p + \mu_b E} = 0. \quad (15)$$

Solving equation (15) for $V_p$ gives the value of $V_p$ at which the assay sensitivity is at its maximum:

$$V_p = \sqrt{\mu_a \mu_b} E \quad (16)$$

Figure 5:
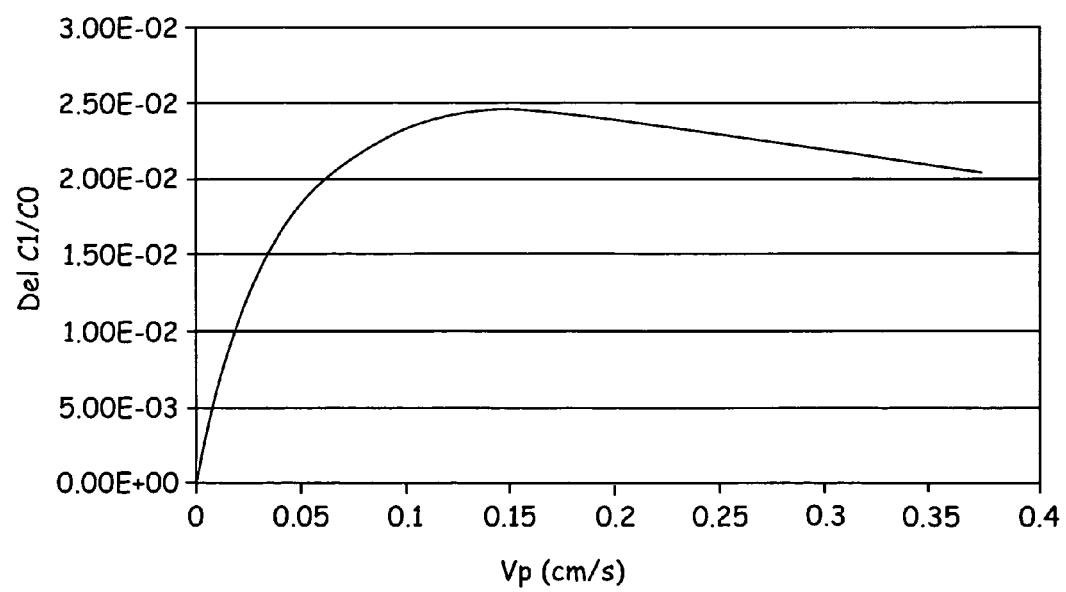
FIG. 5 is a graph constructed from exemplary calculations used to find optimal sensitivity parameters of a pulsed field mobility shift assay.

If in the embodiment of FIG. 4, the electrokinetic mobility of species 'a' were equal to $1.28 \times 10^{-4}$ cm$^2$/vs and the electrokinetic mobility of species 'b' ($\mu_b$) were equal to $1.16 \times 10^{-4}$ cm$^2$/vs, then $\Delta C_1/C_0$ is maximized when the pressure flow ($V_p$) is equal to 0.156 cm/s for a pulsed field E of 1278 V/cm. This is shown in FIG. 5, which shows $\Delta C_1/C_0$ as a function of $V_p$ for that embodiment. FIG. 5 shows there exists a relatively stable plateau region around the point of maximum sensitivity, which means that for that embodiment there is a wide range of pressure driven flow conditions that provide near optimum assay sensitivity.

Optimization of Channel Geometry

Although the channel configuration in the microfluidic device of FIG. 2 is suitable for carrying out embodiments of the invention, the channel configurations can be further optimized to improve the results obtained from embodiments of the invention. Since embodiments of the invention reduce the time required to perform the separation step of a mobility shift assay, the sample being assayed will not have to flow as far down the separation channel 210 as it would have to in a standard (i.e., constant electric field) mobility shift assay. Accordingly, a detector, such as the detector 240 in FIG. 2, can be placed closer to the channel junction where the sample is introduced into the separation channel 210 than a detector 260 suitable for use with a standard mobility shift assay. In the embodiment of FIG. 2, the channel junction where the sample is introduced into the separation channel 210 is at the intersection of channels 212, 216, and 210. The quality of signal resulting from the pulsed field assay depends upon the field distribution near the channel junction. For example, if a sample plug experiences a non-uniform electric field across the cross-section of a microchannel, then the velocity of the charged molecules will be different at different locations across the channel. Hence the signal peak (from the particles) will spread out in time domain and the signal quality will be degraded.

Figure 6A:
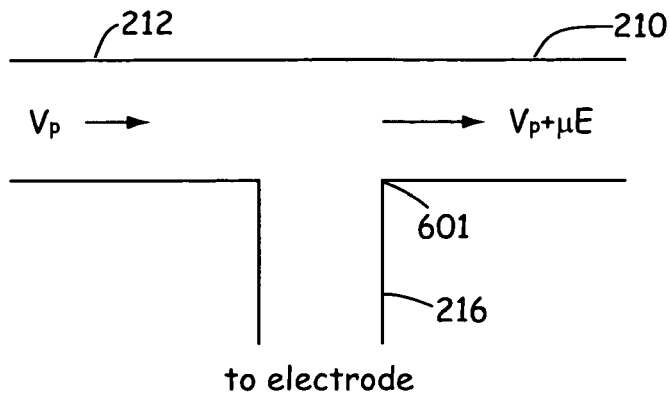
FIG. 6, panels A and B, schematically illustrate an exemplary microfluidic junction channel arrangement suitable for use with pulsed field mobility shift assays.
Figure 6B:
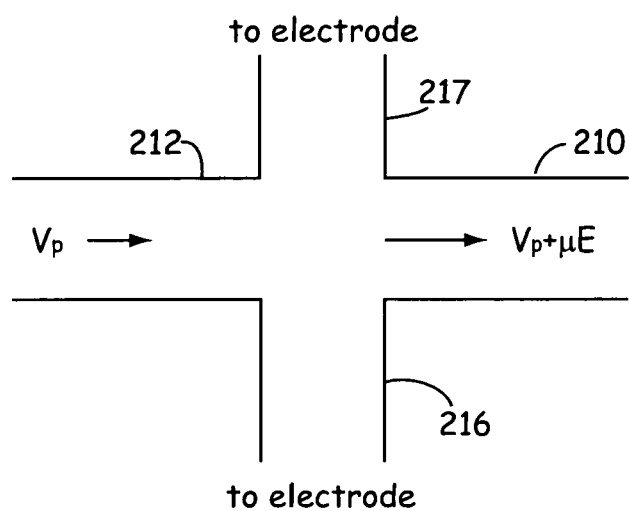

FIG. 6a shows a channel junction similar to the channel junction in FIG. 2 between channels 212, 210, and 216. The electric field being applied to the separation channel 210 results from a voltage applied between electrodes in reservoirs 206 and 208 in FIG. 2. The 90° turn made by the electric field as it turns from channel 216 into channel 210 produces a very non-uniform electric field in the vicinity of the channel junction. The non-uniform electric field is higher near corner 601, and lower on the opposite wall. The non-uniformity seen in the channel junction of FIG. 6a can be reduced by applying the electric field by placing electrodes in reservoirs disposed on opposite sides of the separation channel 210. This could be accomplished by placing electrodes in reservoirs 206 and 207 in FIG. 2, and by fluidly connecting reservoir 207 with separation channel by means of a channel 217 (not shown in FIG. 2). FIG. 6b shows a channel junction that interfaces with two electrode-containing reservoirs through channels 216 and 217. The channel junction in FIG. 6b enhances the uniformity of the electric field across the channel junction, thus improving the results from a pulsed field mobility shift assay. The embodiment of FIG. 6b could be further optimized, however, because the sharp corners at the channel junction still may cause localized high electric field regions.

Figure 7:
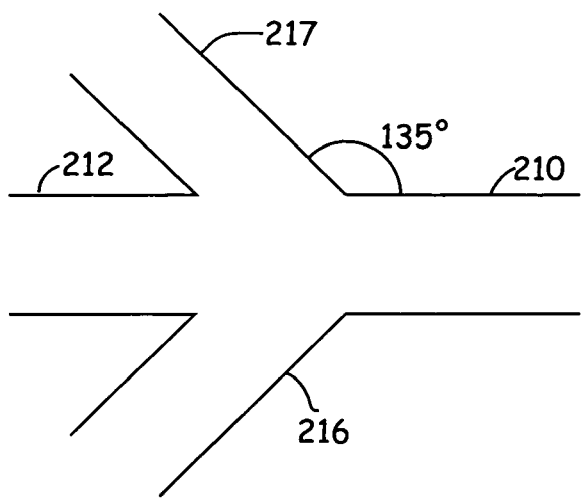
FIG. 7 is a schematic diagram of a channel arrangement suitable for use with pulsed field mobility shift assays.

The angle and width of the two electrode channels 216 and 217 can be varied to further optimize the uniformity of the electric field at the channel junction. FIG. 7 shows one junction geometry thus optimized by means of a numerical simulation of the electric field lines. By varying the side channel geometry and angle, optimized design features for an electrode junction are optionally achieved with a near uniform electric field. The channels leading to electrodes 216, 217 are tilted at an angle of 135°, thus minimizing the high electric field at the corners. Additionally, the width of the reaction channel 212 (59 μm) is less than that the width of the separation channel 210 (74 μm). By creating a near uniform electric field at the channel junction, the results from pulsed field mobility shift assays in accordance with the invention will be improved.

Exemplary Screening Applications

The methods and devices of the present invention can be used to maximize the throughput of microfluidic devices in which serially introduced samples are assayed. The "throughput" of a microfluidic device is typically defined as the number of different materials that can be serially processed by the device per unit time. Materials that are screened at rates greater than 1 material per minute within a single channel of a microfluidic device are generally termed high throughput, while screening of compounds at a rate greater than 1 compound per 10 seconds generally falls into the ultra-high throughput category. Decreasing the amount of time required to perform separations in a microchannel allows the spacing between serially introduced materials to be reduced, thus allowing a greater number of different materials to be serially introduced into the microfluidic device per unit time. The closer that samples are capable of being loaded, the more samples that can be analyzed per unit time.

Spacers and/or buffers are optionally used to keep different reactions separated and/or prevent mixing of samples. For example, a buffer is optionally loaded into a channel after each plug of sample in order to separate samples form one another and prevent contamination between samples. Alternatively, while an enzyme solution may be flowed continuously in a separation channel, different putative substrates may be flowed into the separation channel in plugs. Such plugs are typically separated by materials such as buffers. A sample plug includes an initial sample aliquot and any products produced by incubation or reaction of the initial sample aliquot. The buffer plugs optionally can comprise immiscible fluids to decrease diffusion. Buffer plug lengths are calculated in the same way as sample plug lengths based on considerations such as diffusivity and/or dispersion of the material. For example a buffer plug is typically 500 μm to 5 mm, preferably 600 μm to 3 mm or 850 μm to 1 mm. The last buffer plug loaded or added into a channel or the device is optionally longer, e.g., 500 μm to about 10 mm, to allow for flow pinching.

Figure 8:
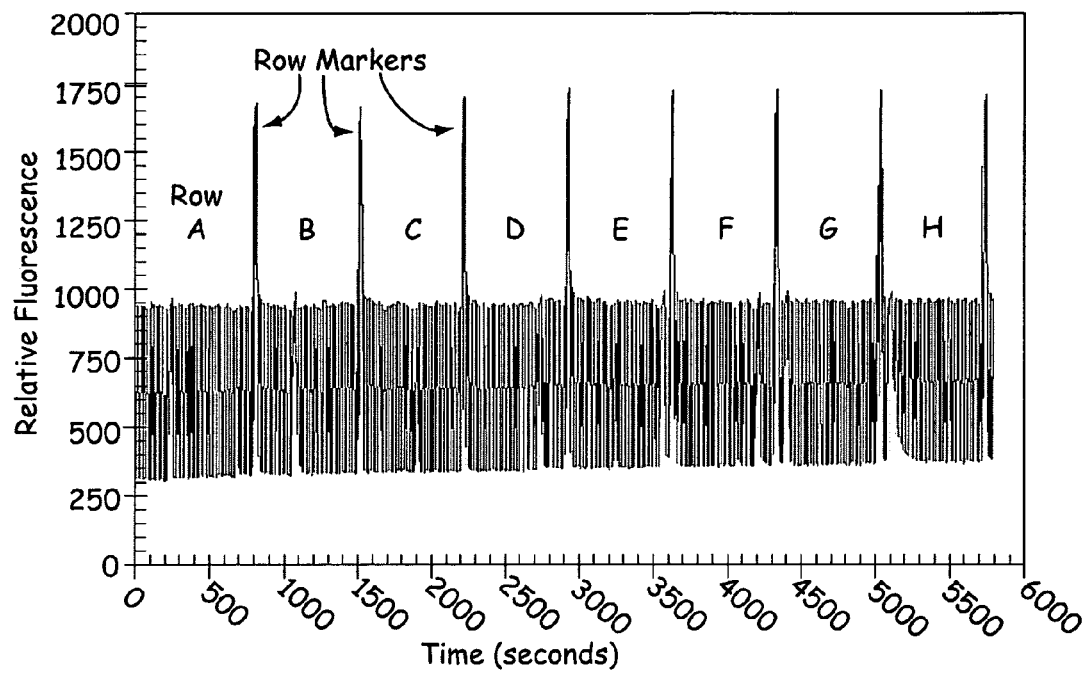
FIG. 8 shows representative data from a mobility shift assay in a high throughput format in accordance with the invention.
Figure 9:
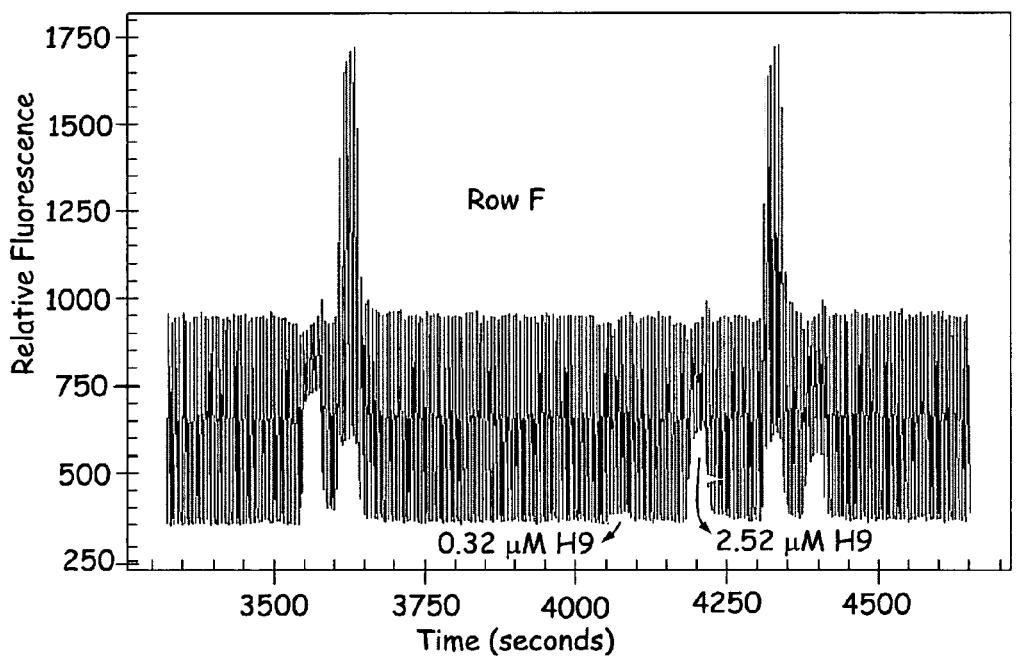
FIG. 9 shows a portion of the data in FIG. 8 in more detail.
Figure 10:
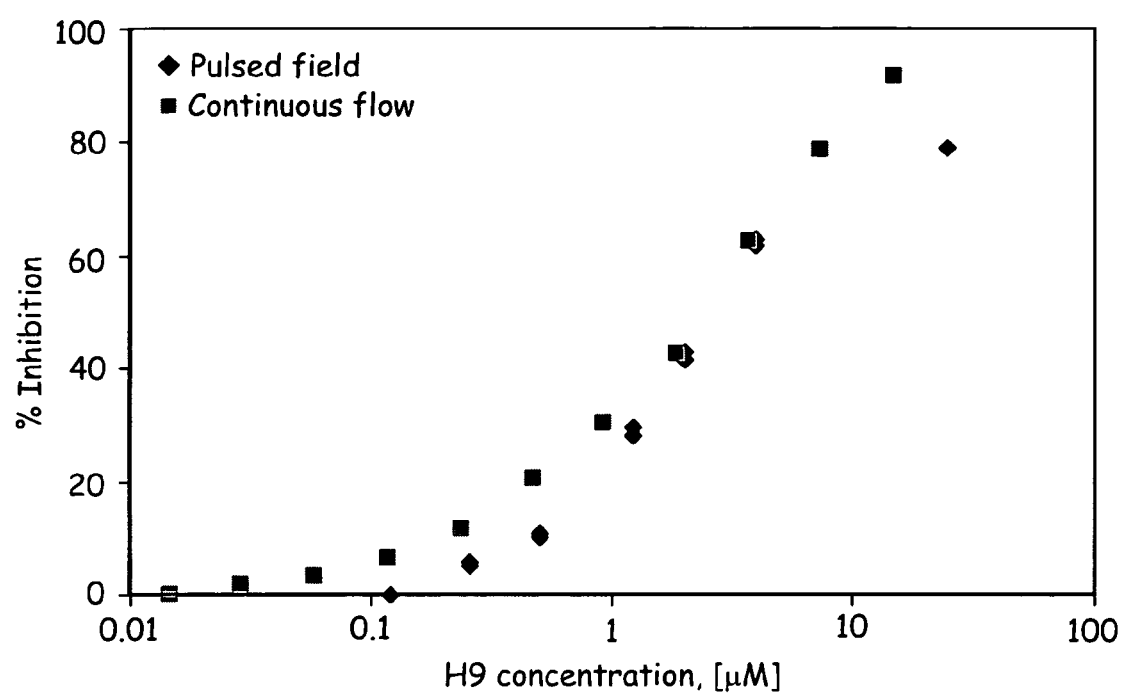
FIG. 10 compares dose response measurements produced by a pulsed field mobility shift assay with measurements produced by a standard mobility shift assay.

In an exemplary embodiment, the pulsed field mobility shift assay was used for screening for Protein Kinase A (PKA) inhibitors. Samples were drawn from a 96 well plate into a microfluidic device through a capillary. The plate contained 7 different concentration samples (0.15 μM, 0.32 μM, 0.63 μM, 1.54 μM, 2.52 μM, 5.05 μM, and 30.75 μM) of H9 at randomly chosen wells. Except for a single well containing the 30.75 μM concentration of H9, two wells contained each of the other six concentrations of H9. The last column of each row of the well plate contained a marker used to indicate the end of row. In this embodiment, the marker was 1 μM of 100% converted PKA product. Once in the reaction channel of the microfluidic device, the pressure driven velocity of the sample was set at 0.028 cm/s and the applied electric field was set to 997 V/cm. FIG. 8 shows the raw data collected for the entire 96 well plate. Each sample was sipped for 30 seconds separated by a 30 second buffer sip. The data from row F in FIG. 8 are shown in more detail in FIG. 9. The data in FIG. 9 clearly shows the change in amplitude of the signal when H9 at the 0.32 and 2.52 μM concentration were sipped from row F of the plate. From the data in FIGS. 8 and 9, the parameter $C_1/C_0$, which is the ratio of the fluorescence measured while the electric field is on to the fluorescence measured while the field is off, was determined for each of the seven H9 concentrations. That parameter was also measured in the absence of H9 to provide a baseline value. The deviation from the baseline value $\Delta C/C = ((C_1/C_0)|_{H9Sample} - (C_1/C_0)|_{buffer})$, was evaluated for each H9 sample. The experimental measurements were then converted to percent inhibition by dividing the $\Delta C/C$ value for a concentration of H9 by the $\Delta C/C$ value corresponding to 100% percent inhibition. These percent inhibition values were used to generate the dose response curve in FIG. 10. The dose response data from the pulsed electric field mobility shift assay (diamonds) were compared to dose response data obtained from a standard (i.e., constant electric field) mobility shift assay (squares). The data from the two methods show remarkable agreement and predict same $K_i$ value for the inhibitor. The $K_i$ value was found to be 3.5 μM. These results clearly show that the pulse field technique can be used to perform high throughput mobility based assays.

Integrated Systems, Methods and Microfluidic Devices of the Invention

The microfluidic devices of the invention can include numerous optional variant embodiments including methods and devices for, e.g., fluid transport, temperature control, detection and the like.

Although the devices and systems specifically illustrated herein are generally described in terms of the performance of a few operations, or of one particular operation (e.g., pulsed field assays), it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein (e.g., upstream and/or downstream of pulsed field separation of fluidic materials as described herein, etc.). Such upstream operations include such operations as sample handling and preparation, e.g., extraction, purification, amplification, cellular activation, labeling reactions, dilution, aliquotting, and the like.

Similarly, downstream operations optionally include similar operations, including, e.g., further separation of sample components, labeling of components, assays and detection operations, electrokinetic or pressure-based injection of components or the like.

The microfluidic devices of the present invention can include other features of microscale systems, such as fluid transport systems which direct particle/fluid movement within and to the microfluidic devices, as well as the flow of fluids to and through various channels or regions, etc. Various combinations of fluid flow mechanisms can be utilized in embodiments of the present invention (e.g., pressure driven flow through the reaction and separation channel regions in FIG. 2). Additionally, various types of fluid flow mechanisms can be utilized in separate areas of microfluidic devices of the invention. For example, the pulsed electrokinetic flow optionally occurs within the separation channel region (210 in FIG. 2) while, e.g., pressure driven flow optionally (and additionally) occurs throughout reaction channel 212 and separation channel 210. Flow of fluidic components such as reagents (e.g., as in to and from the main separation channel), etc., can incorporate any movement mechanism set forth herein (e.g., fluid pressure sources for modulating fluid pressure in microchannels/microreservoirs/etc.; electrokinetic controllers for modulating voltage or current in microchannels/micro-reservoirs/etc.; gravity flow modulators; magnetic control elements for modulating a magnetic field within the microfluidic device; use of hydrostatic, capillary, or wicking forces; or combinations thereof, etc.).

The microfluidic devices of the invention can also include fluid manipulation elements such as parallel stream fluidic converters, i.e., converters which facilitate conversion of at least one serial stream of reagents into parallel streams of reagents for parallel delivery to a reaction site or reaction sites within the device, e.g., as wherein the device has multiple pulse field separation channels or regions. The systems herein optionally include mechanisms such as valve manifolds and a plurality of solenoid valves to control flow switching, e.g., between channels and/or to control pressure/vacuum levels in the, e.g., microchannels. Additionally, molecules, etc. are optionally loaded into one or more channels of a microfluidic device through one sipper capillary fluidly coupled to each of one or more channels and to a sample or particle source, such as a microwell plate.

In the present invention, materials such as proteins, antibodies, enzymes, substrates, buffers, or the like are optionally monitored and/or detected, e.g., the presence of a component of interest can be detected, an activity of a compound can be determined, separation of fluidic materials can be monitored or an effect of a modulator, e.g., on an enzyme's activity, can be measured. Depending upon the detected signal measurements, decisions are optionally made regarding subsequent fluidic operations, e.g., whether to assay a particular component in detail to determine, e.g., kinetic information or, e.g., whether, when, or to what extent to shunt a portion of a fluidic material from a main channel into a second channel (e.g., flowing a fluidic material into a second channel once it has been separated from a mixture of fluidic materials). For example, prior to testing putative substrates against an enzyme in the pulsed field assay, the substrates may be monitored/sorted, etc. and only certain ones directed to be tested against certain enzymes (i.e., in the pulsed field assay).

In brief, the systems described herein optionally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format. For example, the systems herein optionally include a valve manifold and a plurality of solenoid valves to control flow switching between channels and/or to control pressure/vacuum levels in the channels.

Temperature Control

Various embodiments of the present invention can control temperatures to influence numerous parameters or reaction conditions, e.g., those in thermocycling reactions (e.g., PCR, LCR). Additionally, the present invention can control temperatures in order to manipulate reagent properties, etc. In general, and in optional embodiments of the invention, various heating methods can be used to provide a controlled temperature in the involved miniaturized fluidic systems. Such heating methods include both joule and non-joule heating.

Non-joule heating methods can be internal, i.e., integrated into the structure of the microfluidic device, or external, i.e., separate from the microfluidic device. Non-joule heat sources can include, e.g., photon beams, fluid jets, liquid jets, lasers, electromagnetic fields, gas jets, electron beams, thermoelectric heaters, water baths, furnaces, resistive thin films, resistive heating coils, peltier heaters, or other materials, which provide heat to the fluidic system in a conductive manner. Such conductive heating elements transfer thermal energy from, e.g., a resistive element in the heating element to the microfluidic system by way of conduction. Thermal energy provided to the microfluidic system overall, increases the temperature of the microfluidic system to a desired temperature. Accordingly, the fluid temperature and the temperature of the molecules within, e.g., the microchannels of the system, are also increased in temperature. An internal controller in the heating element or within the microfluidic device optionally can be used to regulate the temperature involved. These examples are not limiting and numerous other energy sources can be utilized to raise, control, or modulate, the fluid temperature in the microfluidic device.

Non-joule heating units can attach directly to an external portion of a chip of the microfluidic device. Alternatively, non-joule heating units can be integrated into the structure of the microfluidic device. In either case, the non-joule heating is optionally applied to only selected portions of chips in microfluidic devices (e.g., such as reaction areas, detection areas, etc.) or optionally heats the entire chip of the microfluidic device and provides a uniform temperature distribution throughout the chip. For example, a non-joule heating method optionally only heats the reaction channel area (e.g., region 212 in FIG. 2) so that the correct reaction parameters are set.

A variety of methods can be used to lower fluid temperature in the microfluidic system, through use of energy sinks. Such an energy sink can be a thermal sink or a chemical sink and can be flood, time-varying, spatially varying, or continuous. A thermal sink can include, among others, a fluid jet, a liquid jet, a gas jet, a cryogenic fluid, a super-cooled liquid, a thermoelectric cooling means, e.g., peltier device or an electromagnetic field.

In general, electric current passing through the fluid in a channel produces heat by dissipating energy through the electrical resistance of the fluid. Power dissipates as the current passes through the fluid and goes into the fluid as energy as a function of time to heat the fluid. The following mathematical expression generally describes a relationship between power, electrical current, and fluid resistance: where POWER=power dissipated in fluid; I=electric current passing through fluid; and R=electric resistance of fluid.

$$POWER = I^2 R$$

The above equation provides a relationship between power dissipated ("POWER") to current ("I") and resistance ("R"). In some of the embodiments of the invention, wherein electric current is directed toward moving a fluid (where such is utilized, e.g., in the separation channel region 210 in FIG. 2 where the pulsed fields are used to electrophoretically separate species), a portion of the power goes into kinetic energy of moving the fluid through the channel. Joule heating uses a selected portion of the power to heat the fluid in the channel or a selected channel region(s) of the microfluidic device and can utilize in-channel electrodes. See, e.g., U.S. Pat. No. 5,965,410, which is incorporated herein by reference in its entirety for all purposes. Such a channel region is sometimes narrower or smaller in cross section than other channel regions in the channel structure. The small cross section provides higher resistance in the fluid, which increases the temperature of the fluid as electric current passes therethrough. Alternatively, the electric current can be increased along the length of the channel by increased voltage, which also increases the amount of power dissipated into the fluid to correspondingly increase fluid temperature.

Joule heating permits the precise regional control of temperature and/or heating within separate microfluidic elements of the device of the invention, e.g., within one or several separate channels, without heating other regions where such heating is, e.g., unnecessary or undesirable. For example, joule heating is optionally used within, e.g., a microchannel leading from a well holding a putative substrate to ensure proper temperature for folding, etc., but not within the reaction channel region (e.g., 212 in FIG. 2) or vice versa depending upon the specific reaction conditions. Because the microfluidic elements involved are extremely small in comparison to the mass of the entire microfluidic device in which they are fabricated, such heat remains substantially localized, e.g., it dissipates into and from the device before it affects other fluidic elements. In other words, the relatively massive device functions as a heat sink for the separate fluidic elements contained therein.

To selectively control the temperature of fluid or material of a region of, e.g., a microchannel, the joule heating power supply of the invention can apply voltage and/or current in several optional ways. For instance, the power supply optionally applies direct current (i.e., DC), which passes through one region of a microchannel and into another region of the same microchannel that is smaller in cross section in order to heat fluid and material in the second region. This direct current can be selectively adjusted in magnitude to complement any voltage or electric field applied between the regions to move materials in and out of the respective regions.

In order to heat the material within a region, without adversely affecting the movement of a material, alternating current (i.e., AC) can be selectively applied by a power supply. The AC used to heat the fluid can be selectively adjusted to complement any voltage or electric field applied between regions in order to move fluid into and out of various regions of the device (including the pulsed electric fields used in separation of species). Thus, in options wherein AC is used within the invention, the AC is optionally used in non-pulse field assay areas (e.g., only in reaction areas such as region 210 in FIG. 2, etc.). In some nontypical embodiments, AC is optionally used within any area of the devices of the invention, including within pulsed field separation areas such as region 210 in FIG. 2. However, in the nontypical embodiments wherein AC is used within pulsed field separation regions, the AC field is optionally applied at a much higher frequency than the voltage pulses used for separation of molecules. Thus the AC high frequency response can be filtered out from the low frequency pulsed field signal of interest. Alternating current, voltage, and/or frequency can be adjusted, for example, to heat a fluid without substantially moving the fluid. Alternatively, the power supply can apply a pulse or impulse of current and/or voltage, which will pass through one microchannel region and into another microchannel region to heat the fluid in the region at a given instance in time. This pulse can be selectively adjusted to complement any voltage or electric field applied between the regions in order to move materials, e.g., fluids or other materials, into and out of the various regions. Pulse width, shape, and/or intensity can be adjusted, for example, to heat a fluid substantially without moving the fluid or any materials within the fluid, or to heat the material(s) while moving the fluid or materials. Still further, the power supply optionally applies any combination of DC, AC, and pulse, depending upon the application. The microchannel(s) itself optionally has a desired cross section (e.g., diameter, width or depth) that enhances the heating effects of the current passed through it and the thermal transfer of energy from the current to the fluid (e.g., in addition to, or alternative to, any cross-sectional geometry used to manipulate dispersion rate and/or average velocity of fluidic materials). Again, such above described joule heating is optionally used only in select areas of the present invention and can be entirely separate from, or integrated with the electric pulses used in the pulsed field assays.

Because electrical energy is optionally used to control temperature directly within the fluids contained in the microfluidic devices, the methods and devices of the invention are optionally utilized in microfluidic systems that employ electrokinetic material transport systems, as noted herein. Specifically, the same electrical controllers, power supplies and electrodes can be readily used to control temperature contemporaneously with their control of material transport. See, infra. In some embodiments of the invention, the device provides multiple temperature zones by use of zone heating. On such example apparatus is described in Kopp, M. et al. (1998) "Chemical amplification: continuous-flow PCR on a chip" *Science* 280(5366): 1046-1048.

As can be seen from the above, the elements of the current invention can be configured in many different arrangements depending upon the specific needs of the molecules, etc. under consideration and the parameters of the specific assays/reactions involved. Again, the above non-limiting illustrations are only examples of the many different configurations/embodiments of the invention.

Fluid Flow

A variety of controlling instrumentation and methodology is optionally utilized in conjunction with the microfluidic devices described herein, for controlling the transport and direction of fluidic materials and/or materials within the devices of the present invention by, e.g., pressure-based or electrokinetic control, etc.

In the present system, the fluid direction system controls the transport, flow and/or movement of samples, other reagents, etc. into and through the microfluidic device. For example, the fluid direction system optionally directs the movement of one or more fluid (e.g., samples, buffers) etc. into, e.g., the reaction channel regions, the separation channel regions, etc. The fluid direction system also optionally directs the simultaneous or sequential movement of fluidic materials into one or more channels, etc., e.g., in situations wherein more than one separation channel exits, etc. Additionally, the fluid direction system can optionally direct the shunting of portions of fluidic materials into shunt microchannels and the like.

The fluid direction system also optionally iteratively repeats the fluid direction movements to help create high throughput screening, e.g., of thousands of samples. Alternatively, the fluid direction system optionally repeats the fluid direction movements to a lesser degree of iterations to create a lower throughput screening (applied, e.g., when the specific analysis under observation requires, e.g., a long incubation time when a higher throughput format would be counter productive) or the fluid direction system utilizes a format of high throughput and low throughput screening depending on the specific requirements of the assay, e.g., ancillary actions upstream and/or downstream of the pulsed field assays of the invention, may involve lower throughput activity. Additionally, the devices of the invention optionally use a multiplex format to help achieve high throughput screening, e.g., through use of a series of multiplexed sipper devices or multiplexed system of channels coupled to a single controller for screening in order to increase the amount of samples analyzed in a given period of time. Again, the fluid direction system of the invention optionally controls the flow (timing, rate, etc.) of samples, reagents, buffers, etc. involved in the various optional multiplex embodiments of the invention.

One method of achieving transport or movement of particles through microfluidic devices is by electrokinetic material transport. In general, electrokinetic material transport and direction systems include those systems that rely upon the electrophoretic mobility of charged species within an electric field applied to the structure. Such systems are more particularly referred to as electrophoretic material transport systems. In the current invention, electrokinetic transport is used as the method of fluid transport when species are electrophoretically separated in the pulsed field mobility shift assays (i.e., in the separation channel region) and optionally within other areas of the devices as well, in order to move reagents, etc. to and from various locations of the device. For example, in some embodiments, electrokinetic flow is also applied in, e.g., the separation channel region (see, e.g., FIG. 2). Such electrokinetic flow can be a steady field (or flow) onto which, or on top of which, the pulsed field is applied.

Electrokinetic material transport systems, as used herein, and as optional aspects of the present invention, include systems that transport and direct materials within a structure containing, e.g., microchannels, microreservoirs, etc., through the application of electrical fields to the materials, thereby causing material movement through and among the areas of the microfluidic devices, e.g., cations will move toward a negative electrode, while anions will move toward a positive electrode. Movement of fluids toward or away from a cathode or anode can cause movement of particles suspended within the fluid (or even particles over which the fluid flows). Similarly, the particles can be charged, in which case they will move toward an oppositely charged electrode (indeed, it is possible to achieve fluid flow in one direction while achieving particle flow in the opposite direction). In some embodiments of the present invention, the fluid and/or particles, etc. within the fluid, can be immobile or flowing.

For optional electrophoretic applications of the present invention, the walls of interior channels of the electrokinetic transport system are optionally charged or uncharged. For example, as detailed previously, some separation channel regions are specifically coated to prevent electroosmotic flow within the region. Typical electrokinetic transport systems are made of glass, charged polymers, and uncharged polymers. The interior channels are optionally coated with a material which alters the surface charge of the channel. A variety of electrokinetic controllers are described, e.g., in Ramsey WO 96/04547, Parce et al. WO 98/46438 and Dubrow et al., WO 98/49548 (all of which are incorporated herein by reference in their entirety for all purposes), as well as in a variety of other references noted herein.

To provide appropriate electric fields, the system of the current microfluidic device optionally includes a voltage controller that is capable of applying selectable voltage levels, simultaneously, to, e.g., each of the various microchannels and micro-reservoirs. Such a voltage controller is optionally implemented using multiple voltage dividers and multiple relays to obtain the selectable voltage levels. Alternatively, multiple independent voltage sources are used. For example, different independent voltage sources, etc. are optionally used for the separation channel region where pulsed field assays occur and for all other areas of the device where electrokinetic flow is used for material transport (as opposed to separation). The voltage controller is electrically connected to each of the device's fluid conduits via an electrode positioned or fabricated within each of, or a subset of, the plurality of fluid conduits (e.g., microchannels, microreservoirs, etc.). In one embodiment, multiple electrodes are positioned to provide for switching of the electric field direction in the, e.g., microchannel(s), thereby causing the analytes to travel a longer distance than the physical length of the microchannel. Use of electrokinetic transport to control material movement in interconnected channel structures was described in, e.g., WO 96/94547 to Ramsey. An exemplary controller is described in U.S. Pat. No. 5,800,690. Modulating voltages are concomitantly applied to the various fluid areas of the device to affect a desired fluid flow characteristic, e.g., continuous or discontinuous (e.g., a regularly pulsed field causing the sample to oscillate its direction of travel) flow of labeled components toward a waste reservoir. Particularly, modulation of the voltages applied at the various areas can move and direct fluid flow through the interconnected channel structure of the device.

The controlling instrumentation discussed above is also optionally used to provide for electrokinetic injection or withdrawal of fluidic material downstream of a region of interest to control an upstream flow rate. The same instrumentation and techniques described above are also utilized to inject a fluid into a downstream port to function as a flow control element.

The current invention also optionally includes other methods of fluid transport, e.g., available for situations in which electrokinetic methods are not desirable. See, above. For example, fluid transport and direction, etc. are optionally carried out, in part, in a pressure-based system to, e.g., avoid electrokinetic biasing during sample mixing, e.g., in the reaction channel region before species are separated. Additionally, as described above, pressure based flow or other similar flow such as wicking, etc. is used within the separation channel region as a controllable variable to help optimize the pulsed field electrophoretic separations of the invention. See, above. High throughput systems typically use pressure induced sample introduction. Pressure based flow is also desirable in systems in which electrokinetic transport is also used. For example, as detailed throughout the current invention, pressure based flow is optionally used for introducing and reacting reagents in a system in which the products are electrophoretically separated. In the present invention molecules are optionally loaded and other reagents are flowed through the microchannels or microreservoirs, etc. using, e.g., electrokinetic fluid control and/or under pressure.

Pressure is optionally applied to the microscale elements of the invention, e.g., to a microchannel, microreservoir, region, etc. to achieve fluid movement using any of a variety of techniques. Fluid flow and flow of materials suspended or solubilized within the fluid, including cells or molecules, is optionally regulated by pressure based mechanisms such as those based upon fluid displacement, e.g., using a piston, pressure diaphragm, vacuum pump, probe or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, e.g., a plunger fitted into a material reservoir, for forcing material through a channel or other conduit, or is a combination of such forces. Internal sources include microfabricated pumps, e.g., diaphragm pumps, thermal pumps, lamb wave pumps and the like that have been described in the art. See, e.g., U.S. Pat. Nos. 5,271,724; 5,277,566; and 5,375,979 and Published PCT Application Nos. WO 94/05414 and WO 97/02347.

In some embodiments, a pressure source is applied to a reservoir or well at one end of a microchannel to force a fluidic material through the channel. Optionally, the pressure can be applied to multiple ports at channel termini, or, a single pressure source can be used at a main channel terminus. Optionally, the pressure source is a vacuum source applied at the downstream terminus of the main channel (e.g., well 211 in FIG. 2 which optionally has a vacuum source attached to it to draw samples through the microchannels of the invention) or at the termini of multiple channels. Pressure or vacuum sources are optionally supplied externally to the device or system, e.g., external vacuum or pressure pumps sealably fitted to the inlet or outlet of channels or to the surface openings of micro-reservoirs, or they are internal to the device, e.g., microfabricated pumps integrated into the device and operably linked to channels or they are both external and internal to the device. Examples of microfabricated pumps have been widely described in the art. See, e.g., published International Application No. WO 97/02357.

These applied pressures, or vacuums, generate pressure differentials across the lengths of channels to drive fluid flow through them. In the interconnected channel networks described herein, differential flow rates or volumes are optionally accomplished by applying different pressures or vacuums at multiple ports, or, by applying a single vacuum at a common waste port and configuring the various channels with appropriate resistance to yield desired flow rates. As discussed above, this is optionally done with multiple sources or by connecting a single source to a valve manifold comprising multiple electronically controlled valves, e.g., solenoid valves.

Hydrostatic, wicking and capillary forces are also optionally used to provide fluid flow of materials such as reagents, buffers, etc. in the invention. See, e.g., "Method And Apparatus For Continuous Liquid Flow In Microscale Channels Using Pressure Injection, Wicking And Electrokinetic Injection," by Alajoki et al., U.S. Pat. No. 6,416,642. In using wicking/capillary methods, an adsorbent material or branched capillary structure is placed in fluidic contact with a region where pressure is applied, thereby causing fluid to move towards the adsorbent material or branched capillary structure. Furthermore, the capillary forces are optionally used in conjunction with, e.g., electrokinetic or pressure-based flow in the channels, etc. of the present invention in order to pull fluidic material, etc. through the channels. Additionally, a wick is optionally added to draw fluid through a porous matrix fixed in a microscale channel or capillary.

Use of a hydrostatic pressure differential is another optional way to control flow rates through the channels, etc. of the present invention. For example, in a simple passive aspect, an enzyme suspension is deposited in a reservoir or well at one end of a channel at sufficient volume or height so that the enzyme suspension creates a hydrostatic pressure differential along the length of the channel by virtue of, e.g., the enzyme suspension reservoir having greater height than a well at an opposite terminus of the channel. Typically, the reservoir volume is quite large in comparison to the volume or flow-through rate of the channel, e.g., 10 microliter reservoirs or larger as compared to a 100 micrometer channel cross section.

The present invention optionally includes mechanisms for reducing adsorption of materials during fluid-based flow, e.g., as are described in "Prevention Of Surface Adsorption In Microchannels By Application Of Electric Current During Pressure-Induced Flow", U.S. Pat. No. 6,458,259 by Parce et al. In brief, adsorption of components, proteins, enzymes, markers and other materials to channel walls or other microscale components during pressure-based flow can be reduced by applying an electric field such as an alternating current to the material during flow. Alternatively, flow rate changes due to adsorption are detected and the flow rate is adjusted by a change in pressure or voltage. Such mechanisms are optionally used in areas of the device to, e.g., transport reagents to the reaction channel region (e.g., 212 in FIG. 2) and are optionally not used within separation channel regions (e.g., 210 in FIG. 2). In some embodiments, AC field flow, etc. are optionally used in the separation regions of the invention (e.g., 210 in FIG. 2), however, at a much higher frequency than the pulsed voltages used for the pulsed field assays, thus, the high frequency AC could be filtered out from the lower frequency pulses (i.e., the pulsed signals of interest in the pulsed field assays).

The invention also optionally includes mechanisms for focusing labeling reagents, enzymes, modulators, and other components into the center of microscale flow paths, which is useful in increasing assay throughput by regularizing flow velocity, e.g., in pressure based flow, e.g., as are described in "Focusing Of Microparticles In Microfluidic Systems", U.S. Pat. No. 6,506,609 by H. Garrett Wada et al. In brief, sample materials are focused into the center of a channel by forcing fluid flow from opposing side channels into the main channel, or by other fluid manipulation. Hence, e.g., at the detection regions in FIG. 2, the fluorescent species are focused in the microchannel allowing for better measurements.

In an alternate embodiment, microfluidic systems of the invention can be incorporated into centrifuge rotor devices, which are spun in a centrifuge. Fluids and particles travel through the device due to gravitational and centripetal/centrifugal pressure forces. Such forces, of course, would be used in conjunction with the electrokinetic forces used in the pulsed field separation assays herein.

Fluid flow or particle flow in the present devices and methods is optionally achieved using any one or more of the above techniques, alone or in combination. For example, electrokinetic transport can be used in one area or region of a microfluidic device in order to, e.g., move material through a pulsed field assay region. Additionally, pressure based flow could be used in a different region/area of the same microfluidic device where various fluidic materials (again, e.g., enzymes or the like) are to be transported to a reaction region, etc. Myriad combinations of fluid transport methods can be combined in various embodiments of the present invention depending upon the specific needs of the system/assay being used.

Typically, the controller systems involved are appropriately configured to receive or interface with a microfluidic device or system element as described herein. For example, the controller, optionally includes a stage upon which the device of the invention is mounted to facilitate appropriate interfacing between the controller and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

Detection

In general, detection systems in microfluidic devices include, e.g., optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more microchannels, microchambers, microreservoirs or conduits of the device, such that the detector is within sensory communication with the device, channel, reservoir, or chamber, etc. For example, optical detectors (such as fluorescence detectors) are placed in the detector regions 240 and/or 260 in FIG. 2. Detection systems can be used to, e.g., discern and/or monitor specific reactions, assays, etc. occurring within the microfluidic device, or alternatively, or additionally, to track, e.g., electrophoretic separation of reaction components, etc. in the pulsed field assays. The phrase "proximal," to a particular element or region, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Many different molecular/reaction characteristics can be detected in microfluidic devices of the current invention. For example, various embodiments can detect such things as fluorescence or emitted light, changes in the thermal parameters (e.g., heat capacity, etc.) involved in the assays, etc.

Examples of detection systems in the current invention can include, e.g., optical detection systems for detecting an optical property of a material within, e.g., the microchannels of the microfluidic devices that are incorporated into the microfluidic systems described herein. Such optical detection systems are typically placed adjacent to a microscale channel of a microfluidic device, and optionally are in sensory communication with the channel via an optical detection window or zone that is disposed across the channel or chamber of the device. Again, such a detector is optionally placed at detector 240 in FIG. 2 to measure, e.g., fluorescence from reaction products in the separation channel being separated in a pulsed field assay of the invention.

Optical detection systems of the invention include, e.g., systems that are capable of measuring the light emitted from material within the channel, the transmissivity or absorbance of the material, as well as the material's spectral characteristics, e.g., fluorescence, chemiluminescence, etc. Detectors optionally detect a labeled compound, such as fluorographic, colorimetric and radioactive components. Types of detectors optionally include spectrophotometers, photodiodes, avalanche photodiodes, microscopes, scintillation counters, cameras, diode arrays, imaging systems, photomultiplier tubes, CCD arrays, scanning detectors, galvo-scanners, film and the like, as well as combinations thereof. Proteins, antibodies, or other components that emit a detectable signal can be flowed past the detector, or alternatively, the detector can move relative to an array to determine molecule position (or, the detector can simultaneously monitor a number of spatial positions corresponding to channel regions, e.g., as in a CCD array). For example, a detector (or detectors) could track along separation channel 210 in FIG. 2 as various fluorescent components are pulsed through the channel. Examples of suitable detectors are widely available from a variety of commercial sources known to persons of skill. See, also, *The Photonics Design and Application Handbook*, books 1, 2, 3 and 4, published annually by Laurin Publishing Co., Berkshire Common, P.O. Box 1146, Pittsfield, Mass. for common sources for optical components.

As noted above, the present devices optionally include, as microfluidic devices typically do, a detection window or zone at which a signal, e.g., fluorescence, is monitored. This detection window or zone optionally includes a transparent cover allowing visual or optical observation and detection of the assay results, e.g., observation of a colorimetric, fluorometric or radioactive response, or a change in the velocity of calorimetric, fluorometric or radioactive component.

Another optional embodiment of the present invention involves use of fluorescence correlation spectroscopy and/or confocal nanofluorimetric techniques to detect fluorescence from the molecules in the microfluidic device. Such techniques are easily available (e.g., from Evotec, Hamburg, Germany) and involve detection of fluorescence from molecules that diffuse through the illuminated focus area of a confocal lens. The length of any photon burst observed will correspond to the time spent in the confocal focus by the molecule. Various algorithms used for analysis can be used to evaluate fluorescence signals from individual molecules based on changes in, e.g., brightness, fluorescence lifetime, spectral shift, FRET, quenching characteristics, etc.

The sensor or detection portion of the devices and methods of the present invention can optionally comprise a number of different apparatuses. For example, fluorescence can be detected by, e.g., a photomultiplier tube, a charge coupled device (CCD) (or a CCD camera), a photodiode, or the like.

A photomultiplier tube is an optional aspect of the current invention. Photomultiplier tubes (PMTs) are devices which convert light (photons) into electronic signals. The detection of each photon by the PMT is amplified into a larger and more easily measurable pulse of electrons. PMTs are commonly used in many laboratory applications and settings and are well known to those in the art.

Another optional embodiment of the present invention comprises a charge-coupled device. CCD cameras can detect even very small amounts of electromagnetic energy (e.g., such that emitted by fluorophores in the present invention). CCD cameras are made from semi-conducting silicon wafers that release free electrons when light photons strike the wafers. The output of electrons is linearly directly proportional to the amount of photons that strike the wafer. This allows the correlation between the image brightness and the actual brightness of the event observed. CCD cameras are very well suited for imaging of fluorescence emissions since they can detect even extremely faint events, can work over a broad range of spectrum, and can detect both very bright and very weak events. CCD cameras are well know to those in the art and several suitable examples include those made by:

Stratagene (La Jolla, Calif.), Alpha-Innotech (San Leandro, Calif.), and Apogee Instruments (Tucson, Ariz.) among others.

Yet another optional embodiment of the present invention comprises use of a photodiode to detect fluorescence from molecules in the microfluidic device. Photodiodes absorb incident photons that cause electrons in the photodiode to diffuse across a region in the diode thus causing a measurable potential difference across the device. This potential can be measured and is directly related to the intensity of the incident light.

In some aspects, the detector measures an amount of light emitted from the material, such as a fluorescent or chemiluminescent material. As such, the detection system will typically include collection optics for gathering a light based signal transmitted through the detection window or zone, and transmitting that signal to an appropriate light detector. Microscope objectives of varying power, field diameter, and focal length are readily utilized as at least a portion of this optical train. The detection system is typically coupled to a computer (described in greater detail below), via an analog to digital or digital to analog converter, for transmitting detected light data to the computer for analysis, storage and data manipulation.

In the case of fluorescent materials such as labeled enzymes or products or fluorescence indicator dyes or molecules, the detector optionally includes a light source that produces light at an appropriate wavelength for activating the fluorescent material, as well as optics for directing the light source to the material contained in the channel. The light source can be any number of light sources that provides an appropriate wavelength, including lasers, laser diodes and LEDs. Other light sources are optionally utilized for other detection systems. For example, broadband light sources for light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with a computer (described below), by permitting the use of few or a single communication port(s) for transmitting information between the controller, the detector and the computer. Integration of the detection system with a computer system typically includes software for converting detector signal information into assay result information, e.g., separation of species, concentration of a substrate, concentration of a product, presence of a compound of interest, interaction between various samples, or the like.

Computer

As noted above, any of the fluid direction system, the detection system, the electric pulse generator, etc. as well as other aspects of the current invention described herein (e.g., temperature control, etc.), are optionally coupled to an appropriately programmed processor or computer that functions to instruct the operation of these instruments in accordance with preprogrammed or user input instructions, receive data and information from these instruments, and interpret, manipulate and report this information to a user. As such, the computer is typically appropriately coupled to one or more of the appropriate instruments (e.g., including an analog to digital or digital to analog converter as needed).

The computer optionally includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the operation of, e.g., the fluid direction controller, electric pulse generator, etc. to carry out the desired operation.

For example, the computer is optionally used to direct a fluid direction system to control fluid flow, e.g., into and through a variety of interconnected microchannels (e.g., into and through the various microchannels of the invention, such as the separation channels comprising pulsed electric flow, etc.). Additionally, the fluid direction system optionally directs fluid flow controlling which samples are contacted with each other and/or with various reagents, buffers, etc. in, e.g., a reaction region or other region(s) in the microfluidic device. Furthermore, the fluid direction system optionally controls the coordination of movements of multiple fluids/molecules/etc. concurrently as well as sequentially. For example, the computer optionally directs the fluid direction system to direct the movement of at least a first member of a plurality of molecules into a first member of a plurality of microchannels concurrent with directing the movement of at least a second member of the plurality of molecules into one or more detection channel regions. For example, different samples can be separated in different pulsed field separation channels. Additionally or alternatively, the fluid direction system directs the movement of at least a first member of the plurality of molecules into the plurality of microchannels concurrent with incubating at least a second member of the plurality of molecules or directs movement of at least a first member of the plurality of molecules into the one or more detection or pulsed field channel regions concurrent with incubating at least a second member of the plurality of molecules.

By coordinating channel switching, the computer controlled fluid direction system directs the movement of at least one member of the plurality of molecules into the plurality of microchannels and/or one member into a detection region at a desired time interval, e.g., greater than 1 minute, about every 60 seconds or less, about every 30 seconds or less, about every 10 seconds or less, about every 1.0 seconds or less, or about every 0.1 seconds or less. Each sample, with appropriate channel switching as described above, remains in the plurality of channels for a desired period of time, e.g., between about 0.1 minutes or less and about 60 minutes or more. For example, samples optionally remain in the reaction channels for a selected incubation time of, e.g., 2 minutes.

The computer then optionally receives the data from the one or more sensors/detectors included within the system, e.g., detector 240 in FIG. 2, interprets the data, and either provides it in a user understood format, or uses that data to initiate further controller instructions, in accordance with the programming, e.g., such as in monitoring and control of flow rates (e.g., as involved in separation of materials through pulsed field analysis in the separation channel region), temperatures, applied voltages, pressures, and the like.

In the present invention, the computer typically includes software for the monitoring and control of materials in the various microchannels, etc. For example, the software directs electric field pulses to control and direct flow as described above. Additionally the software is optionally used to control electrokinetic, pressure-modulated, or the like, injection or withdrawal of material. The computer also typically provides instructions, e.g., to the controller or fluid direction system for switching flow between channels to help achieve a high throughput format.

In addition, the computer optionally includes software for deconvolution of the signal or signals from the detection system. For example, the deconvolution distinguishes between two detectably different spectral electrophoretic mobilities that were both detected, e.g., when label intensity levels were measured in the separation channel.

Any controller or computer optionally includes a monitor, which is often a cathode ray tube ("CRT") display, a flat panel display (e.g., active matrix liquid crystal display, liquid crystal display), or the like. Data produced from the microfluidic device, e.g., fluorographic indication of selected molecules, is optionally displayed in electronic form on the monitor. Additionally, the data gathered from the microfluidic device can be outputted in printed form. The data, whether in printed form or electronic form (e.g., as displayed on a monitor), can be in various or multiple formats, e.g., curves, histograms, numeric series, tables, graphs and the like.

Computer circuitry is often placed in a box which includes, e.g., numerous integrated circuit chips, such as a microprocessor, memory, interface circuits, etc. The box also optionally includes such things as a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

Exemplary Integrated System

Figure 11:
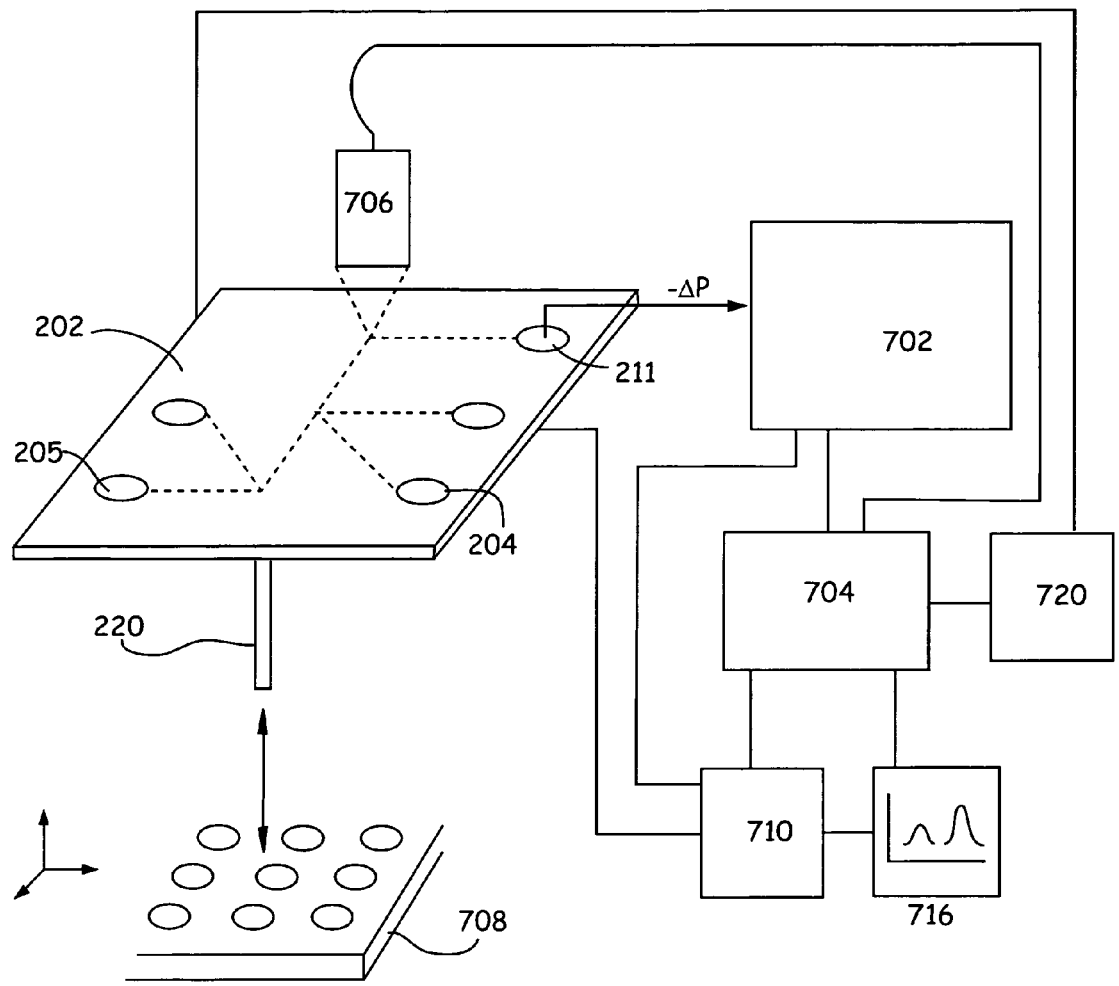
FIG. 11 is a schematic view of an integrated system comprising a microfluidic device incorporating an embodiment of a pulsed field mobility shift assay in accordance with the invention.

FIG. 11 provides additional details regarding an exemplary integrated system that may be used with embodiments of the pulsed field assay devices and methods of the invention. As shown, microfluidic device 202 has main separation channel 210 disposed therein (e.g., a separation channel wherein pulsed field assays occur). As depicted, the integrated system optionally includes pipettor channel 220 protruding from microfluidic device 202 for accessing a source of materials external to the microfluidic system. In FIG. 11, the external source is a multiwell plate 708. A sample can be flowed from pipettor channel 220 by applying a vacuum at reservoir 211 (or another point in the system), by applying appropriate wicking arrangements, or by applying an electric field to the pipettor channel to induce electrokinetic flow. Additional materials, such as buffer solutions, substrate solutions, enzyme solutions, test molecules, fluorescence indicator dyes or molecules and the like, can be flowed from reservoirs such as 204 or 205 and thence into a reaction channel and a separation channel.

Detector 706 is in sensory communication with a separation channel in the microfluidic device 202 so that it can detect signals emanating from labeled materials flowing through the detection region. Detector 706 is optionally coupled to any of the channels or regions of the device where detection is desired. Detector 706 is operably linked to computer 704, which digitizes, stores, and manipulates signal information detected by detector 706.

Fluid direction system 702 controls voltage, pressure, etc. (or a combination of such), e.g., at the wells of the systems or through the channels of the system, or at vacuum couplings fluidly coupled to main separation channel 210, or any other channel described above. Optionally, as depicted, computer 704 controls fluid direction system 702. In one set of embodiments, computer 704 uses signal information to select further parameters for the microfluidic system. For example, upon detecting the interaction between a particular sample and a first reagent, the computer optionally directs addition of a second reagent of interest (e.g., a reaction inhibitor) into the system to be tested against that particular sample. In some embodiments, this same direction system controls the timing and strength of the pulsed electric fields in separation channel 210 (e.g., through computer 704). In other embodiments the pulsed fields are generated through a separate device, e.g., 720.

Temperature control system 710 controls joule and/or non-joule heating at, e.g., the wells of the systems or through the channels of the system as described herein. Optionally, as depicted, computer 704 controls temperature control system 710. In one set of embodiments, computer 704 uses signal information to select further parameters for the microfluidic system. For example, upon detecting the desired temperature in a sample in, e.g., reaction channel 212, the computer optionally directs addition of, e.g., a potential binding molecule, etc. into the system to be tested against one or more samples.

Monitor 716 displays the data produced by the microfluidic device, e.g., graphical representation of, e.g., separation or non-separation of fluidic materials, interaction (if any) between samples, reagents, test molecules, etc. Optionally, as depicted, computer 704 controls monitor 716. Additionally, computer 704 is connected to and directs additional components such as printers, electronic data storage devices and the like.

Assay Kits

The present invention also provides kits for utilizing the microfluidic devices of the invention to perform pulsed field mobility shift assays, etc. In particular, these kits typically include microfluidic devices, systems, modules and workstations, etc. A kit optionally contains additional components for the assembly and/or operation of a multimodule workstation of the invention including, but not restricted to robotic elements (e.g., a track robot, a robotic armature, or the like), plate handling devices, fluid handling devices, and computers (including e.g., input devices, monitors, c.p.u., system software to analyze mobility shift data from pulsed field assays, and the like).

Generally, the microfluidic devices described herein are optionally packaged to include some or all reagents for performing the device's functions (e.g., the reagents used in pulsed field assays). For example, the kits can optionally include any of the microfluidic devices described along with assay components, buffers, reagents, enzymes, serum proteins, receptors, sample materials, antibodies, substrates, control material, spacers, buffers, immiscible fluids, etc., for performing the pulsed field assays as well as other ancillary and/or additional actions such as separations, etc. using the methods/devices of the invention. In the case of prepackaged reagents, the kits optionally include pre-measured or pre-dosed reagents that are ready to incorporate into the assays without measurement, e.g., pre-measured fluid aliquots, or pre-weighed or pre-measured solid reagents that can be easily reconstituted by the end-user of the kit.

Such kits also typically include appropriate instructions for using the devices and reagents, and in cases where the reagents (or all necessary reagents) are not predisposed in the devices themselves, with appropriate instructions for introducing the reagents into the channels/chambers/reservoirs/etc. of the device. In this latter case, these kits optionally include special ancillary devices for introducing materials into the microfluidic systems, e.g., appropriately configured syringes/pumps, or the like (in some embodiments, the device itself comprises a pipettor element, such as an electropipettor for introducing material into channels/chambers/reservoirs/etc. within the device). In the former case, such kits typically include a microfluidic device with necessary reagents predisposed in the channels/chambers/reservoirs/etc. of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (e.g., enzymatic inhibitors, microbicides/bacteriostats, anticoagulants, etc.), the physical stabilization of the material, e.g., through immobilization on a solid support, entrapment in a matrix (e.g., a bead, a gel, etc.), lyophilization, or the like.

The elements of the kits of the present invention are typically packaged together in a single package or set of related packages. The package optionally includes written instructions for utilizing one or more device of the invention, e.g., primarily the pulsed field assays, in accordance with the methods described herein. Kits also optionally include packaging materials or containers for holding the microfluidic device, system or reagent elements.

The discussion above is generally applicable to the aspects and embodiments of the invention described herein. Moreover, modifications are optionally made to the methods and devices described herein without departing from the spirit and scope of the invention as claimed, and the invention is optionally put to a number of different uses including the following:

The use of a microfluidic system containing at least a first substrate and having a first channel and a second channel intersecting the first channel, at least one of the channels having at least one cross-sectional dimension in a range from 0.1 to 500 micrometer, in order to test the effect of each of a plurality of test compounds on a biochemical system through use of a pulsed field mobility shift assay.

The use of a microfluidic system as described herein, wherein a biochemical system flows through one of said channels substantially continuously, providing for, e.g., sequential testing of a plurality of test compounds. Such as continuous pulsed field assays.

The use of a microfluidic device as described herein to monitor reactions within microchannels/microchambers/reservoirs/etc.

The use of electrokinetic injection in a microfluidic device as described herein to modulate or achieve flow in the channels.

The use of a combination of wicks, hydrostatic pressure, electrokinetic injection and pressure based flow elements in a microfluidic device as described herein to modulate, focus, or achieve flow of materials, e.g., in the channels of the device.

The use of pulsed field electrokinetic flow to achieve separation of molecules based upon their respective electrophoretic mobility.

An assay utilizing a use of any one of the microfluidic systems or substrates described herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of detecting an interaction between a first molecule and at least a second molecule in a microfluidic device, the method comprising:

flowing a first labeled molecule with a first electrophoretic mobility through at least a first microchannel, wherein flowing of the first molecule comprises a continuous injection of the first molecule;

flowing at least a second molecule with a second electrophoretic mobility through the microchannel, wherein flowing of the second molecule comprises an intermittent injection of the second molecule at a first frequency;

applying a pulsed electric field through the microchannel, wherein the pulsed electric field separates the first and at least second molecule based upon the electrophoretic mobilities of the molecules;

adjusting the pressure induced velocity or electrokinetic mobility of the two molecules to optimize a measurement of assay sensitivity by maximizing a value of $\Delta C_1/C_o$, wherein $\Delta C_1$ is the difference in concentration of the two molecules when the pulsed field is on and $C_o$ is the concentration of one of the molecules when the pulsed field is off; and detecting a level of label or a level of signal from a label in the microchannel over a select time period.

2. The method of claim 1, wherein the at least second molecule comprises a second molecule and at least a third molecule.

3. The method of claim 2, wherein the first molecule comprises a first component of a receptor-ligand pair, the second molecule comprises a second component of the receptor-ligand pair, and the at least third molecule comprises the receptor-ligand pair.

4. The method of claim 2, wherein the first molecule comprises a first component of an antibody-antigen pair, the second molecule comprises a second component of the antibody-antigen pair, and the at least third molecule comprises the antibody-antigen pair.

5. The method of claim 2, wherein the first molecule comprises a first component of an at least partially complementary double-stranded nucleic acid, the second molecule comprises a second component of the at least partially complementary double-stranded nucleic acid, and the at least third molecule comprises a double-stranded nucleic acid comprising the first and second components.

6. The method of claim 2, wherein the first molecule comprises a substrate, the second molecule comprises an enzyme and the at least third molecule comprises a product.

7. The method of claim 6, wherein the product comprises the label of the first molecule.

8. The method of claim 6, wherein the product comprises the first molecule, wherein such molecule comprises a changed electrophoretic mobility.

9. The method of claim 1, wherein the at least second molecule comprises a derivative form of the first molecule.

10. The method of claim 2, further comprising at least a fourth molecule, wherein the fourth molecule comprises one or more of: a reaction enhancer, a reaction inhibitor, or a reaction competitor.

11. The method of claim 2, wherein a size of one or more of: the first molecule, the second molecule, the third molecule, or the fourth molecule changes after the interaction.

12. The method of claim 2, wherein a charge of one or more of: the first molecule, the second molecule, the third molecule, or the fourth molecule, changes after the interaction.

13. The method of claim 2, wherein an electrophoretic mobility of one or more of: the first molecule, the second molecule, the third molecule, or the fourth molecule, changes after the interaction.

14. The method of claim 1, wherein the interaction comprises one or more of: an enzymatic reaction or a binding reaction.

15. The method of claim 1, wherein flowing comprises use of one or more of: electrophoretic transport, electroosmotic transport, pressure based transport, wicking based transport, or hydrostatic pressure based transport.

16. The method of claim 1, wherein flowing comprises incubating the first and at least second molecule together for a specific period of time.

17. The method of claim 1, wherein the label comprises one or more of: a fluorescent label, a chemiluminescent label, or a radioactive label.

18. The method of claim 1, wherein the electrophoretic mobility of the first molecule is greater than the electrophoretic mobility of the at least second molecule.

19. The method of claim 1, wherein the electrophoretic mobility of the first molecule is lesser than the electrophoretic mobility of the at least second molecule.

20. The method of claim 1, wherein the at least second molecule comprises a label.

21. The method of claim 20, wherein the label of the at least second molecule comprises a same label type as the label of the first molecule.

22. The method of claim 20, wherein the label of the at least second molecule comprises a different label type than the label of the first molecule.

23. The method of claim 1, wherein applying a pulsed electric field comprises applying a first specific voltage or electric current through the microchannel for a first specific period of time followed by applying a second specific voltage or electric current for a second specific period of time.

24. The method of claim 23, wherein the first and second periods of time are equal.

25. The method of claim 24, wherein the first and second time periods comprise from at least about 0.1 second to about 20 seconds or more, from at least about 0.5 seconds to about 15 seconds or more, from at least 1 second to at least about 10 seconds or more, or from at least about 5 seconds to at least about 7 seconds or more.

26. The method of claim 23, wherein the first and second periods of time are not equal.

27. The method of claim 26, wherein the first and second time period differ by a factor of about 1, of about 2, of about 3, of about 4, of about 5, of about 10, of about 25, or of about 50.

28. The method of claim 23, wherein the first and second specific voltages or electric currents comprise from at least about 10 V/cm to about 3,000 V/cm or more, from at least about 50 V/cm to about 2,000 V/cm or more, from at least about 100 V/cm to at least about 1,000 V/cm or more, or from at least about 250 V/cm to at least about 750 V/cm or more.

29. The method of claim 23, wherein the first and second specific periods of time are selectively set in relation to the flowing of the second molecule into the microchannel and wherein the flowing of the second molecule into the microchannel comprises a third specific period of time.

30. The method of claim 29, wherein the first or second period of time is from at least about 1 to about 100 or more, from at least about 5 to at least about 75, from at least about 10 to at least about 50, or from at least about 25 to at least about 45 times shorter than the third period of time.

31. The method of claim 1, wherein detecting comprises determining reaction kinetics for the interaction between the first molecule and the at least second molecule.

32. The method of claim 1, wherein the at least first microchannel comprises one or more of: a polymer gel, a microfabricated barrier, or a sieving matrix.

* * * * *